United States Patent
Freundlich et al.

(10) Patent No.: US 11,186,549 B2
(45) Date of Patent: Nov. 30, 2021

(54) THERAPEUTIC INDAZOLES

(71) Applicant: RUTGERS, THE STATE UNIVERSITY OF NEW JERSEY, New Brunswick, NJ (US)

(72) Inventors: Joel S. Freundlich, New Brunswick, NJ (US); David Alland, New Brunswick, NJ (US); Matthew B. Neiditch, New Brunswick, NJ (US); Pradeep Kumar, New Brunswick, NJ (US); Glenn Capodagli, New Brunswick, NJ (US); Divya Awasthi, New Brunswick, NJ (US); Sean Ekins, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/642,817

(22) PCT Filed: Aug. 29, 2018

(86) PCT No.: PCT/US2018/048611
§ 371 (c)(1),
(2) Date: Feb. 27, 2020

(87) PCT Pub. No.: WO2019/046467
PCT Pub. Date: Mar. 7, 2019

(65) Prior Publication Data
US 2020/0199076 A1  Jun. 25, 2020

Related U.S. Application Data

(60) Provisional application No. 62/551,534, filed on Aug. 29, 2017.

(51) Int. Cl.
*C07D 231/56* (2006.01)
*A61P 31/06* (2006.01)
*A61K 31/4409* (2006.01)

(52) U.S. Cl.
CPC ........ *C07D 231/56* (2013.01); *A61K 31/4409* (2013.01); *A61P 31/06* (2018.01)

(58) Field of Classification Search
None
See application file for complete search history.

(56) References Cited

U.S. PATENT DOCUMENTS

| | | | |
|---|---|---|---|
| 4,695,581 A | 9/1987 | Suzuki et al. | |
| 6,355,628 B1 | 3/2002 | Schwendner et al. | |
| 7,199,147 B2 * | 4/2007 | Imazaki | A61P 11/06 514/394 |
| 7,217,722 B2 * | 5/2007 | Takami | A61P 9/12 514/307 |
| 8,772,305 B2 | 7/2014 | Dahmann et al. | |
| 9,718,840 B2 | 8/2017 | Ikuma et al. | |
| 2004/0106667 A1 | 6/2004 | Damour et al. | |
| 2008/0004268 A1 | 1/2008 | Nguyen et al. | |
| 2010/0093703 A1 | 4/2010 | Wagner et al. | |

FOREIGN PATENT DOCUMENTS

| | | | | |
|---|---|---|---|---|
| WO | 2004037251 A1 | 5/2004 | | |
| WO | WO-2006052189 A1 * | 5/2006 | ................ | A61P 9/10 |
| WO | 2006067392 A2 | 6/2006 | | |
| WO | WO-2011103202 A2 * | 8/2011 | ........... | C07D 417/14 |
| WO | 2019046465 A2 | 3/2019 | | |

OTHER PUBLICATIONS

Portevin, D., et al., "A polyketide synthase catalyzes the last condensation step of mycolic acid biosynthesis in mycobacteria and related organisms", Proc Natl Acad Sci USA 101, 314-319 (2004).

Saunders, N, et al., "Deep resequencing of serial sputum isolates of Mycobacterium tuberculosis during therapeutic failure due to poor compliance reveals stepwise mutation of key resistance genes on an otherwise stable genetic background", J Infect 62, 212-217 (2011).

Schiebel, J., et al., "Structural basis for the recognition of mycolic acid precursors by KasA, a condensing enzyme and drug target from Mycobacterium tuberculosis", J Biol Chem 288, 34190-34204 (2013).

Singh, V, et al., "The β-Ketoacyl-ACP Synthase from Mycobacterium tuberculosis as Potential Drug Targets", Current Medicinal Chemistry 18(9), 1318-1324 (2011).

Tahlan, K, et al., "SQ109 targets MmpL3, a membrane transporter of trehalose monomycolate involved in mycolic acid donation to the cell wall core of Mycobacterium tuberculosis", Antimicrob Agents Chemother 56, 1797-1809 (2012).

Wilson, R, et al., "Antituberculosis thiophenes define a requirement for Pks13 in mycolic acid biosynthesis", Nat Chem Biol, 2013, 9, 499-506.

(Continued)

*Primary Examiner* — Zinna Northington Davis

(74) *Attorney, Agent, or Firm* — Viksnins Harris Padys Malen LLP

(57) ABSTRACT

The invention provides compounds of formula (I): and salts thereof wherein $R^1$-$R^5$ have any of the meanings described in the specification. The compounds are useful for treating bacterial infections (e.g. tuberculosis).

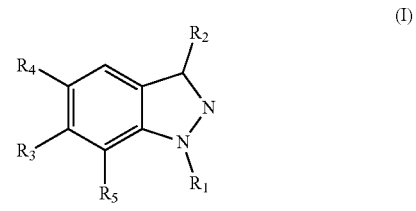

12 Claims, 17 Drawing Sheets

(56) References Cited

OTHER PUBLICATIONS

"Global Tuberculosis Report—2016", 1-214, Geneva: World Health Organization (2016).
Abrahams, K., et al., "Identification of KasA as the cellular target of an anti-tubercular scaffold", Nature Communications 7 (12581), 13 pages (2016).
Alland, D., et al., "Characterization of the Mycobacterium tuberculosis iniBAC promoter, a promoter that responds to cell wall biosynthesis inhibition", J Bacteriol 182, 1802-1811 (2000).
Ananthan, S., et al., "High-throughput screening for inhibitors of Mycobacterium tuberculosis H37Rv", Tuberculosis (Edinb) 89, 334-353 (2009).
Ballell, L., et al., "Fueling Open-Source Drug Discovery: 177 Small-Molecule Leads against Tuberculosis", ChemMedChem 8, 313-321 (2013).
Banerjee, A., et al., "inhA, a Gene Encoding a Target for Isoniazid and Ethionamide in Mycobacterium tuberculosis", Science 263, 227-230 (1994).
Banerjee, A., et al., "The mabA gene from the inhA operon of Mycobacterium tuberculosis encodes a 3-ketoacyl reductase that fails to confer isoniazid resistance", Microbiology 144 (Pt 10), 2697-2704 (1998).
Bhatt, A., et al., "Conditional Depletion of KasA, a Key Enzyme of Mycolic Acid Biosynthesis, Leads to Mycobacterial Cell Lysis", J Bacteriol 187, 7596-7606 (2005).
Bhatt, A., et al., "The Mycobacterium tuberculosis FAS-II condensing enzymes: their role in mycolic acid biosynthesis, acid-fastness, pathogenesis and in future drug development", Mol Microbiol 64, 1442-1454 (2007).
Bloemberg, G., et al., "Acquired Resistance to Bedaquiline and Delamanid in Therapy for Tuberculosis", Engl J Med 373, 1986-1988 (2015).
Brown, A.K., et al., "Platensimycin Activity against Mycobacterial b-Ketoacyl—ACP Synthases", PLoS One 4, e6306, 10 pages (2009).
Database Chemabs, Accession No. 1046454-30-1, 1 page (2008).
Database Chemabs, Accession No. 110327-56-5, 1 page (1987).
Database Chemabs, Accession No. 1183812-20-5, 1 page (2009).
Database Chemabs, Accession No. 1378308-23-6, 1 pages (2012).
Database Chemabs, Accession No. 1621383_91_2, 1 page (2014).
Database Chemabs, Accession No. 1621383-88-7, 1 page (2014).
Database Chemabs, Accession No. 353539-35-2, 1 page (2001).
Database Chemabs, Accession No. 454188-51-3, 1 page (2002).
Database Chemabs, Accession No. 45441-11-9, 1 page (2002).
Database Chemabs, Accession No. 478826-83-1, 1 page (2003).
Database Chemabs, Accession No. 478826-85-6, 1 page (2003).
Database Chemabs, Accession No. 478827-14-1, 1 page (2003).
Database Chemabs, Accession No. 478828-54-5, 1 page (2003).
Database Chemabs, Accession No. 478828-56-7, 1 page (2003).
Database Chemabs, Accession No. 47883_92_6, 1 page (2003).
Database Chemabs, Accession No. 478830-42-1, 1 page (2003).
Database Chemabs, Accession No. 64151-38-8, 1 page (1984).
Database Chemabs, Accession No. 778621-17-3, 1 page (2004).
Database Chemabs, Accession No. 778622-22-3, 1 page (2004).
Database Chemabs, Accession No. 88369-87-3, 1 page (1984).
Database Chemabs, Accession No. 886625-06-5, 1 page (2006).
Database Chemabs, Accession No. 925590-76-7, 1 page (2007).
Database Chemabs, Accession No. 940881-63-0, 1 page (2007).
Database Chemabs, Accession No. 953390-47-1, 1 page (2007).
Dubnau, E., et al., "Oxygenated mycolic acids are necessary for virulence of Mycobacterium tuberculosis in mice", Mol Microbiol 36, 630-637 (2000).
Foster, A., "Deuterium isotope effects in the metabolism of drugs and xenobiotics: implications for drug design", Advances in Drug Reseach 14, 1-40 (1985).
Gelmanova, I., et al., "Barriers to successful tuberculosis treatment in Tomsk, Russian Federation: non-adherence, default and the acquisition of multidrug resistance", Bull World Health Organ 85, 703-711 (2007).
Glickman, M.S., et al., "A novel mycolic acid cyclopropane synthetase is required for cording, persistence, and virulence of Mycobacterium tuberculosis", Mol Cell 5, 717-727 (2000).
Inoyama, D, et al., "A Preclinical Candidate Targeting Mycobacterium tuberculosis KasA", Cell Chemical Biology 27, 560-570 (2020).
Kapilashrami, K., et al., "Thiolactomycin-based β-Ketoacyl-AcpM Synthase A (KasA) Inhibitors[S]", J Biol Chem 288(9), 6045-6052 (2013).
Kumar, P., et al., "Synergistic Lethality of a Binary Inhibitor of Mycobacterium tuberculosis KasA", mbio.asm.org 9(6), e02101-17, 23 pages (2018).
Lee, W., et al., "Elucidation of the protonation states of the catalytic residues in mtKasA—Implications for inhibitor design", Biochemistry 50, 5743-5756 (2011).
Lin, J., et al., "An alarming rate of drug-resistant tuberculosis at Ngwelezane Hospital in Northern KwaZulu Natal, South Africa", Int J Tuberc Lung Dis 8, 568-573 (2004).
Low, J., et al., "Screening of TB Actives against Nontuberculous Mycobacteria Delivers High Hit Rates", Frontiers in Microbiology 8, 1539, 9 pages and Supplementary Material, 2 pages (2017).
Machutta, C.A., et al., "Slow Onset Inhibition of Bacterial β-Ketoacyl-acyl Carrier Protein Synthases by Thiolactomycin", J Biol Chem 285, 6161-6169 (2010).
Maddry, J, et al., "Antituberculosis Activity of the Molecular Libraries Screening Center Network Library", Tuberculosis 89(5), 354-363 (2009).
Pablos-Mendez, A, et al., "Nonadherence in tuberculosis treatment: predictors and consequences in New York City", Am J Med 102, 164-170 (1997).
Patent Cooperation Treaty, International Searching Authority, Search Report and Written Opinion for PCT/US2018/048611, 18 pages, dated Jan. 8, 2019.
Cunningham et al., "Exploring the SAR of the β-Ketoacyl-ACP Synthase Inhibitor GSK3011724A and Optimization around a Genotoxic Metabolite", ACS Infect Dis 6, 1098-1109 (2020).
Database Chemabs, Accession No. 1152873_01_2, 1 page (2009).

* cited by examiner

Table 1.

| Strain | Type | Resistance | DG167 MIC (µM) | INH MIC (µM) |
|---|---|---|---|---|
| H37Rv | Laboratory | Susceptible | 0.39 | 0.4 |
| M. bovis BCG | Laboratory | Susceptible | 0.39 | 0.4 |
| Mtb DRM5 (Tahlan et al., 2012) | Laboratory | SQ109, DA5a | 0.39 | 0.4 |
| Mtb DRM8.3 (Tahlan et al., 2012) | Laboratory | SQ109, DA8a | 0.39 | 0.4 |
| Mtb mc$^2$4914 (Vilcheze et al., 2006) | Laboratory | INH | 0.78 | 1.6 |
| Mtb DRM12$^b$ | Laboratory | INH | 0.39 | 0.4 |
| Mtb 210 | Clinical | Susceptible | 0.39 | 0.4 |
| Mtb TDR692 | Clinical | Susceptible | 0.39 | 0.2 |
| Mtb TDR31 | Clinical | INH, RIF, EMB, KAN, SM, CAP | 0.2 | >12 |
| Mtb TDR36 | Clinical | INH, RIF, EMB | 0.39 | >12 |
| Mtb TDR116 | Clinical | INH, EMB, PAS | 0.2 | >12 |
| M. smegmatis | Laboratory | Wild-type | >50 | >12 |
| M. abcessus | ATCC | Wild-type | >50 | >12 |
| M. avium | ATCC | Wild-type | >50 | >12 |
| M. fortuitum | ATCC | Wild-type | >50 | >12 |
| M. marinum | ATCC | Wild-type | >50 | >12 |

FIG. 1

Table 2.

| kasA-SNP | H37-Rv | DRM-167-16x3 | DRM-167-8x6 | DRM-167-8x3 | DRM-167-16x6 | DRM-167-8x2 | DRM-167-32x11 | DRM-167-32x2 |
|---|---|---|---|---|---|---|---|---|
| | none | gTc-gCc | Atg-Ttg | aTc-aCc | aTt-aGt | Gcc-Acc | Ggc-Agc | Ccc-Acc |
| KasAa | none | V123A | M213L | I145T | I122S | A119T | G240S | P206T |
| DG167 (MIC, µM) | 0.39 | 1.56 | 3.12 | 6.25 | 50 | 50 | 100 | >100 |
| INH (MIC, µM) | 0.19 | 0.38 | 0.38 | 0.38 | 0.19 | 0.38 | 0.19 | 0.19 |
| RIF (MIC, µM) | 0.001 | 0.001 | 0.001 | 0.002 | 0.001 | 0.001 | 0.001 | 0.001 |
| EMB (MIC, µM) | 0.78 | 1.56 | 1.56 | 1.56 | 1.56 | 1.56 | 1.56 | 1.56 |
| ETH (MIC, µM) | 25 | 25 | 25 | 25 | 12.5 | 12.5 | 12.5 | 12.5 |
| Moxi (MIC, µM) | 0.03 | 0.03 | 0.03 | 0.03 | 0.03 | 0.03 | 0.03 | 0.03 |
| BDQ (MIC, µM) | 1 | 0.5 | 0.5 | 1 | 0.5 | 0.5 | 0.25 | 0.12 |
| PA824 (MIC, µM) | 0.1 | 0.1 | 0.1 | 0.1 | 0.1 | 0.1 | 0.1 | 0.1 |
| SQ109 (MIC, µM) | 0.8 | 0.8 | 0.4 | 0.8 | 0.4 | 0.8 | 0.4 | 0.4 | a: row indicates amino acid substitution corresponding to kasA-SNPs.

FIG. 2

Table 3.

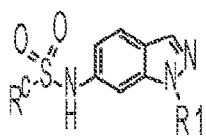

| Ex | R¹ | Rc | Mtb H37Rv MIC (µM) | Vero Cell CC$_{50}$ (µM) | MLM stability t$_{1/2}$ (min) (without NADPH)* | MLM stability Clint (µL/min/mg protein) | Kinetic solubility in pH 7.4 PBS (µM) |
|---|---|---|---|---|---|---|---|
| 1 | H | n-Bu | >100 | nd | 12.2 (>3060) | 68.7 | >600 |
| 2 | Et | n-Bu | 6.2 | 44.4 | 1.29 (>3060) | 536 | 472 |
| 3 | n-Pr | n-Bu | >100 | nd | 0.753 (>3060) | 921 | 130 |
| 4 | i-Pr | n-Bu | >100 | nd | 0.878 (>3060) | 789 | >500 |
| 5 | Ph | n-Bu | >100 | nd | 0.505 (>3060) | 1370 | 33.7 |
| 6 | Bn | n-Bu | >100 | nd | 2.88 (>3060) | 241 | 33.8 |
| 7 | Me | Me | >100 | nd | nd | nd | nd |
| 8 | Me | Et | >100 | nd | nd | nd | nd |
| 9 | Me | n-Pr | 12.5 | nd | nd | nd | nd |
| 10 | Me | i-Pr | >100 | nd | nd | nd | nd |
| 11 | Me | n-Pen | 0.20 | >100 | nd | nd | nd |
| 12 | Me | n-Hex | >100 | >170 | nd | nd | nd |
| 13 | Me | NC(CH$_2$)$_4$ | 3.1 | >100 | nd | nd | nd |
| 14 | Me | MeO(CH$_2$)$_4$ | >100 | >100 | nd | nd | nd |
| 15 | Me | MeO(CH$_2$)$_2$CH(Me)(CH$_2$)$_2$ | >100 | nd | nd | nd | nd |
| 16 | Me | Me(CH$_2$)$_2$CH(Et) | >100 | >100 | nd | nd | nd |
| 17 | Me | Me(CH$_2$)$_2$CH(Me) | >100 | >100 | nd | nd | nd |
| 18 | Me | (Me)$_2$CH(CH$_2$)$_3$ | >100 | nd | nd | nd | nd |
| 19 | Me | p-MeC$_6$H$_5$ | 50 | nd | nd | nd | nd |
| 20 | Me | Bn | >100 | nd | nd | nd | nd |
| 21 | Me | PhC$_2$H$_4$ | >100 | 19.8 | nd | nd | nd |
| 22 | Me | cyclopropyl | >100 | nd | nd | nd | nd |
| 23 | Me | cyclobutyl | >100 | nd | nd | nd | nd |
| 24 | Me | cyclopentyl | >100 | nd | nd | nd | nd |
| 25 | Me | cyclohexyl | 12.5 | nd | nd | nd | nd |
| 26 | Me | 4-CF$_3$-cyclohexyl | >100 | nd | nd | nd | nd |
| 27 | Me | piperidinyl | >100 | nd | nd | nd | nd |
| 28 | Me | C$_6$H$_{12}$CH$_2$ | >100 | nd | nd | nd | nd |
| 29 | CD$_3$ | n-Bu | 0.39 | 180 | 16.8 (>3060) | 41.3 | >500 |
| 30 | CD$_3$ | n-Pen | 0.20 | >100 | nd | nd | nd |
| 31 | CD$_3$ | MeOCH2(CH$_2$)$_3$ | >100 | >100 | nd | nd | nd |

*MLM t$_{1/2}$ in min without NADPH is shown in bracket

FIG. 3A

| Ex | Structure | Mtb H37Rv MIC (µM) | Vero Cell CC50 (µM) | MLM stability t1/2 (min) (without NADPH)* | MLM stability Clint (µL/min/mg protein) | Kinetic solubility in pH 7.4 PBS (µM) |
|---|---|---|---|---|---|---|
| 32 | (structure) | >100 | nd | nd | nd | nd |
| 33 | (structure) | 3.1 | 25 | 1.17 (>3060) | 595 | 131 |
| 34 | (structure) | >100 | nd | nd | nd | nd |
| 35 | (structure) | >100 | nd | 1.29 | 536 | 472 |
| 36 | (structure) | >100 | nd | 0.668 (13.1) | 1040 | >500 |
| 37 | (structure) | >100 | 110 | 1.16 | 597 | >500 |
| 38 | (structure) | >100 | 6.7 | nd | nd | nd |
| 39 | (structure) | >100 | 25 | nd | nd | nd |
| 40 | (structure) | >100 | nd | 12.2 (>3060) | 56.7 | >500 |
| 41 | (structure) | 0.2 | 94 | 11.5 | 60.3 | 76.8 |

FIG. 3B

| | | | | | | |
|---|---|---|---|---|---|---|
| 42 | ![structure] | 0.125 | 89 | 3.26 | 212 | 476 |
| 43 | ![structure] | 0.2 | 175 | 28.4 | 24.4 | 438 |
| 44 | ![structure] | 0.25 | 160 | | | |
| 45 | ![structure] | 0.39 | 22 | 32.1 | 21.6 | 443 |
| 46 | ![structure] | 0.39 | 170 | | | |
| 47 | ![structure] | 0.2 | 160 | | | |
| 48 | ![structure] | 0.2 | 150 | | | |
| 49 | ![structure] | >100 | >170 | | | |
| 50 | ![structure] | >100 | >160 | | | |
| 51 | ![structure] | 25 | 78 | | | |
| 52 | ![structure] | 12 | 37 | | | |
| 53 | ![structure] | 3.1 | >160 | | | |

*MLM t1/2 in min without NADPH is shown in bracket

FIG. 4

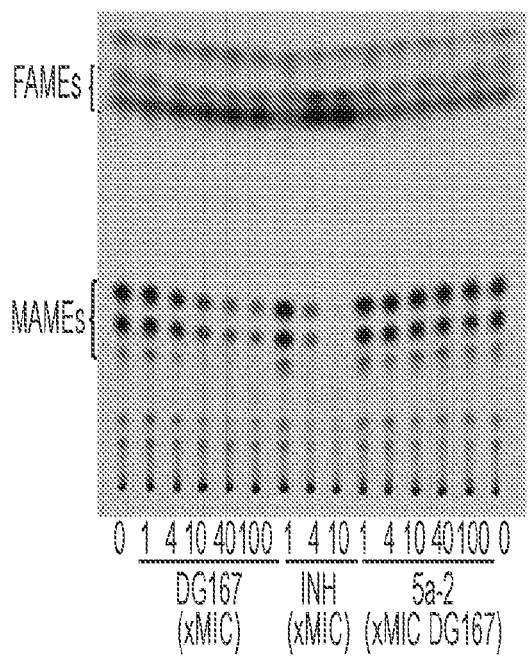 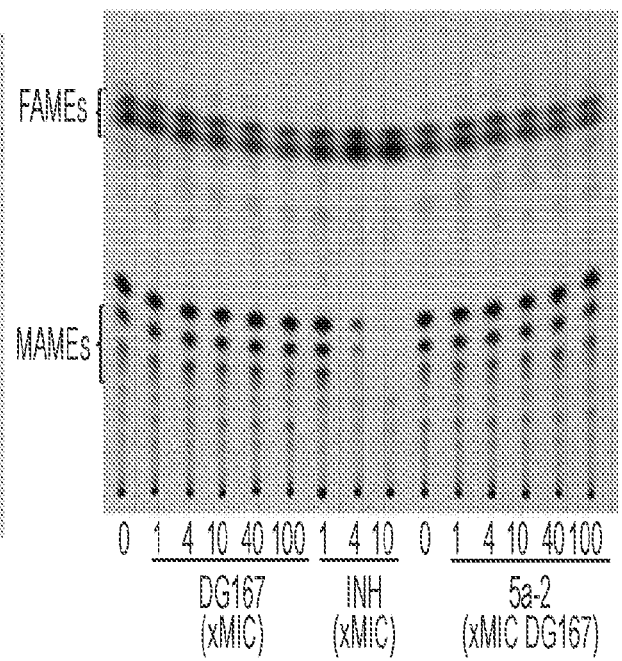
FIG. 4A　　　　　　　　　FIG. 4B
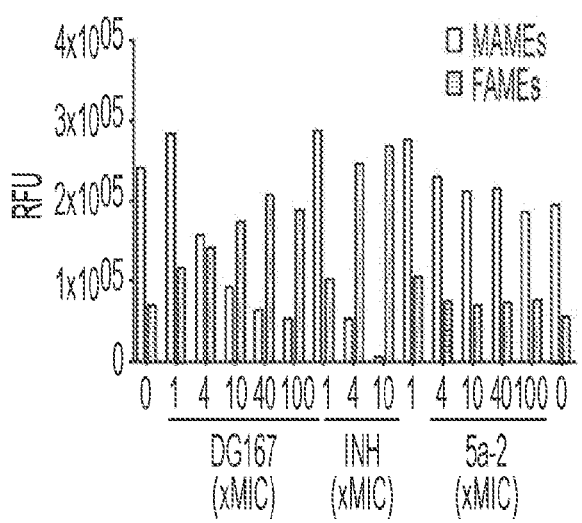 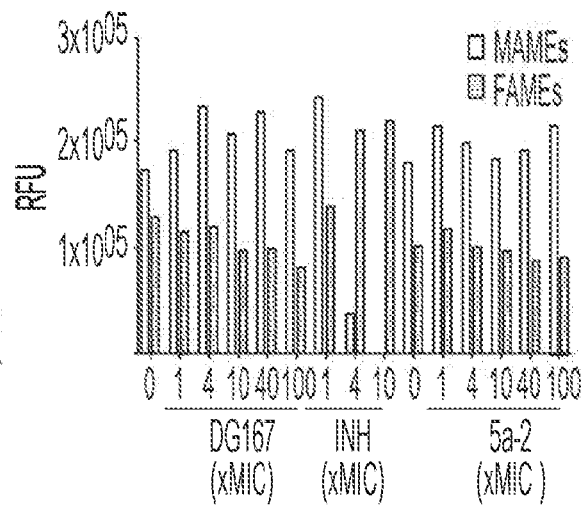
FIG. 4C　　　　　　　　　FIG. 4D

| Mouse # | Starting Weight (g) | Ended Weights(g) | Observation | Pathology |
|---|---|---|---|---|
| 1 | 30 | 30 | Normal Active | Liver- Normal size, color and appearance<br><br>Kidneys & Spleen- normal appearance |
| 2 | 22 | 24 | Normal Active | Liver- Normal size, color and appearance<br><br>Kidneys & Spleen-normal appearance |
| 3 | 25 | 28 | Normal Active | Liver- Normal size, color and appearance<br><br>Kidneys & Spleen-normal appearance |
| 4 | 24 | 26 | Normal Active | Liver- Normal size, color and appearance<br><br>Kidneys & Spleen-normal appearance |
| 5 | 28 | 28 | Normal Active | Liver- Normal size, color and appearance<br><br>Kidneys & Spleen-normal appearance |

FIG. 9

| Example | Kin. Sol. (pH 7.4 PBS, μM) | MLM t1/2 (min) | MLM Clint (μL/min mg protein) |
|---|---|---|---|
| 41 | 76.8 | 11.5 | 60.3 |
| 42 | 476 | 3.26 | 212 |
| 43 | 175 | 28.4 | 24.4 |
| 45 | 443 | 32.1 | 21.6 |

FIG. 11

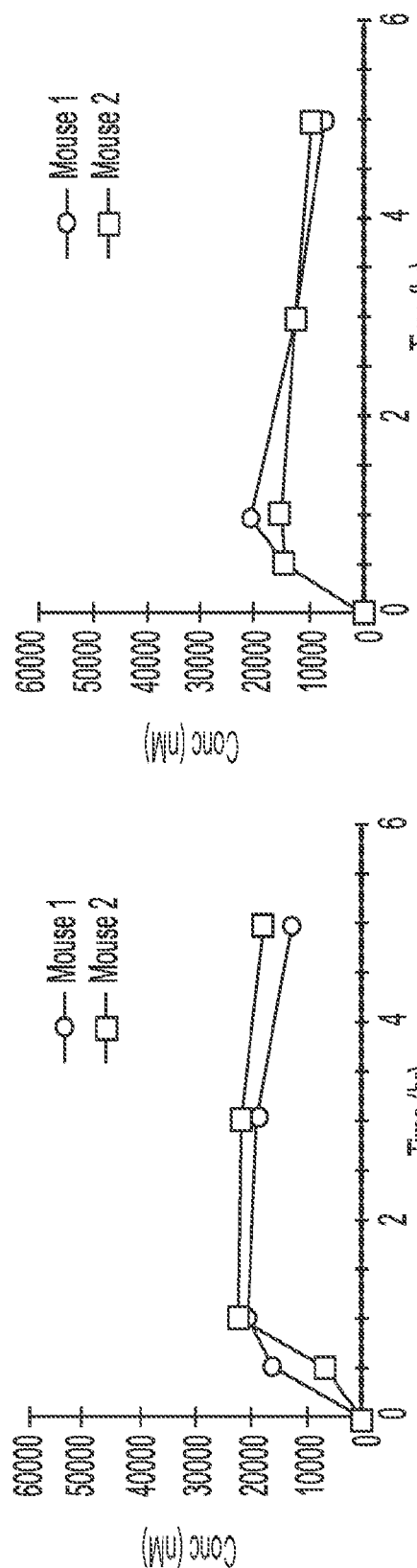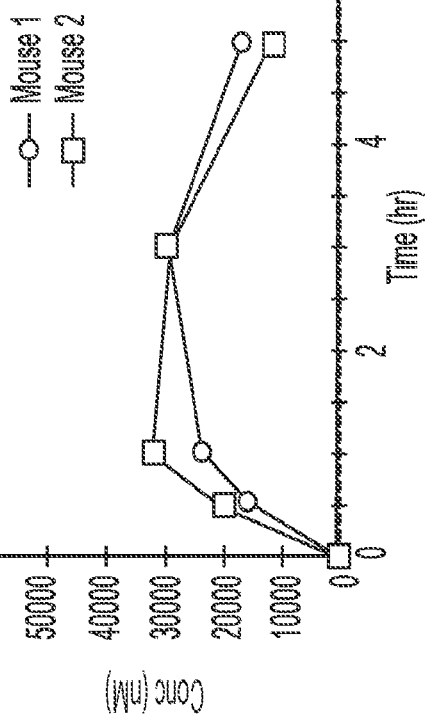

THERAPEUTIC INDAZOLES

PRIORITY

This application claims priority from U.S. Provisional Patent Application No. 62/551,534, filed 29 Aug. 2017. The entire content of this application is incorporated herein by reference.

GOVERNMENT FUNDING

This invention was made with government support under 1U19AI109713, R21AI111647, and R33AI11167 awarded by the National Institutes of Health. The government has certain rights in the invention.

BACKGROUND

Tuberculosis (TB) is an ongoing global health threat, made worse by an increase in drug-resistant *Mycobacterium tuberculosis* (TB) (Lin, J., et al., *Int J Tuberc Lung Dis*, 2004, 8, 568-573). The development of new TB drugs has not kept pace with drug-resistance. Clinical drug-resistance has been identified among even the most recently approved drugs bedaquiline (BDQ) and delamanid (Bloemberg, G. V., et al., *Engl J Med*, 2015, 373, 1986-1988), prompting concerns that TB may become untreatable. TB regimens require lengthy treatment—six months for drug susceptible TB and >18 months for drug-resistance TB. A lengthy treatment duration provides ample opportunity for partial non-compliance that can lead to both treatment failure and the emergence of new drug-resistance (Gelmanova, I. Y., et al., *Bull World Health Organ*, 2007, 85, 703-711; Pablos-Mendez, A., et al., *Am J Med*, 1997, 102, 164-170; and Saunders, N.J., et al., *J Infect*, 2011, 62, 212-217). Thus, new TB therapies are needed to both counter emerging drug-resistance and to enable shortened TB treatments (Global tuberculosis report 2016 (Geneva: World Health Organization)).

Renewed efforts to find new anti-TB leads have led to the discovery of thousands of whole cell active compounds and novel chemotypes. Many of these compounds are undergoing optimization to deliver a lead for further drug development (Ananthan, S et al., *Tuberculosis (Edinb)*, 2009, 89, 334-353; Ballell, L., et al., *Chem Med Chem*, 2013, 8, 313-321; and Maddry, J. A., et al., *Tuberculosis (Edinb)*, 2009, 89, 354-363). The cell-wall is well established to be one of the most vulnerable subcellular components of bacteria including *M. tuberculosis*. Inhibitors of cell-wall biosynthesis disrupt the outer cell-envelope causing rapid cell death, and a number of drugs that target the cell-wall such as isoniazid (INH), ethambutol (EMB), ethionamide (ETH), carbapenems and delamanid are effective at treating clinical TB. Furthermore, many of the enzymes involved in biosynthesis of the *M. tuberculosis* cell-wall do not have close homologues in humans, suggesting that specific inhibitors of this pathway would be less toxic. A screen for selecting cell-wall specific anti-tuberculars using a whole-cell reporter that signaled transcriptional induction of the iniBAC operon that is specifically induced by cell-wall inhibitors has previously been described (Alland, D., *J Bacteriol*, 2000, 182, 1802-1811). This screen led to the discovery of the thiophenes as inhibitors of polyketide synthase 13 (Pks13) (Wilson et al., 2013) and DA5/DA8 that inhibited MmpL3 (Tahlan, K., et al., *Antimicrob Agents Chemother*, 2012, 56, 1797-1809).

The mycobacterial cell-wall is adorned with essential mycolic acids, which are synthesized by a fatty acid synthase-II (FAS-II) system that is absent in humans. The FAS-II complex consists of five enzymes encoded in two operons: one operon encoding three enzymes β-ketoacyl-ACP synthases KasA and KasB, an acyl-carrier protein (AcpM) and the second operon encoding the ketoreductase (MabA) and the enoyl reductase (InhA) (Banerjee, A., et al., *Science*, 1994, 263, 227-230; and Banerjee, A., et al., *Microbiology*, 1998, 144 (Pt 10), 2697-2704). This complex carries out cyclic elongation of short-chain fatty acids to produce long-chain meromycolic acids ($C_{48}$-$C_{64}$) (Bhatt, A., et al., *J Bacteriol*, 2005, 187, 7596-7606) that are condensed with $C_{26}$ fatty acids to yield branched mycolic acids by Pks13 (Portevin, D., et al., *Proc Natl Acad Sci USA*, 2004, 101, 314-319; and Wilson, R., et al., *Nat Chem Biol*, 2013, 9, 499-506). Mycolic acid variants are not only critical for pathogenesis, virulence, and persistence (Bhatt, A., et al., *Mol Microbiol*, 2007, 64, 1442-1454; Dubnau, E., et al., *Mol Microbiol*, 2000, 36, 630-637; and Glickman, M. S., et al., *Mol Cell*, 2000, 5, 717-727), but they are also effective targets for anti-TB drugs. For example, INH, one of the most effective first-line anti-tubercular drugs, targets InhA. KasA has also been shown to be essential and a vulnerable target in mycobacteria (Bhatt, A., et al., *Mol Microbiol*, 2007, 64, 1442-1454). Unfortunately, previously known inhibitors of KasA/KasB, thiolactomycin (TLM) (Kapilashrami, K., et al., *J Biol Chem*, 2013, 288, 6045-6052; Lee, W., et al., *Biochemistry*, 2011, 50, 5743-5756; Machutta, C. A., et al., *J Biol Chem*, 2010, 285, 6161-6169; and Schiebel, J., et al., *J Biol Chem*, 2013, 288, 34190-34204) and platensimycin (Brown, A. K., et al., *PLoS One*, 2009, 4, e6306) have very poor whole-cell activity in *M. tuberculosis* of 142 and 27 µM, respectively.

Currently there is a need for agents and methods that are useful for treating bacterial infections such as tuberculosis.

SUMMARY

Small molecule indazole sulfonamides have been synthesized and demonstrated to be potent inhibitors of *Mycobacterium tuberculosis* in culture and more specifically to be inhibitors of the *M. tuberculosis* enzyme KasA. Representative molecules in these classes exhibit acceptable physiochemical, in vitro ADME, and mouse PK profiles. Select molecules have been crystallized with KasA and their binding modes to the target protein have been elucidated. Select molecules have exhibited in vivo activity in a mouse model of acute *M. tuberculosis* infection. DG167 has also exhibited in vivo synergy with isoniazid in a mouse model of acute *M. tuberculosis* infection.

Accordingly, in one embodiment the invention provides a compound of formula I:

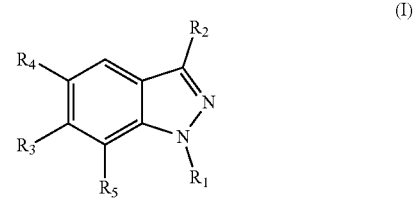

or a salt thereof, wherein:

R$^1$ is H, (C$_1$-C$_4$)alkyl, phenyl, or benzyl;

R$^2$ is H, halo, or (C$_1$-C$_4$)alkyl that is optionally substituted with one or more halo;

R$^3$ is H and R$^4$ is —N(R$^a$)SO$_2$R$^c$, —N(R$^a$)C(=S)N(R$^a$)R$^c$, —N(R$^a$)C(=O)R$^c$, —N(R$^a$)C(=O)OR$^c$, —N(R$^a$)R$^d$, or —N(R$^a$)C(=O)N(R$^a$)R$^c$; or R$^3$ is —N(R$^a$)SO$_2$R$^c$, —N(R$^a$)C(=S)N(R$^a$)R$^c$, —N(R$^a$)C(=O)R$^c$, —N(R$^a$)C(=O)OR$^c$, —N(R$^a$)R$^d$, or —N(R$^a$)C(=O)N(R$^a$)R$^c$ and R$^4$ is H;

R$^5$ is H, (C$_1$-C$_4$)alkyl, or halo;

each R$^a$ is independently H or (C$_1$-C$_4$)alkyl;

R$^c$ is (C$_3$-C$_6$)cycloalkyl, piperidinyl, or (C$_2$-C$_6$)alkyl, wherein any (C$_3$-C$_6$)cycloalkyl and (C$_2$-C$_6$)alkyl is optionally substituted with one or more groups independently selected from the group consisting of halo, (C$_3$-C$_6$)cycloalkyl, phenyl, (C$_1$-C$_4$)alkoxy, trifluoromethyl, and cyano; and R$^d$ is (C$_3$-C$_6$)cycloalkyl, or (C$_2$-C$_6$)alkyl, wherein any (C$_3$-C$_6$)cycloalkyl and (C$_2$-C$_6$)alkyl is optionally substituted with one or more groups independently selected from the group consisting of halo, (C$_3$-C$_6$)cycloalkyl, phenyl, (C$_1$-C$_4$)alkoxy, trifluoromethyl, and cyano; provided the compound is not:

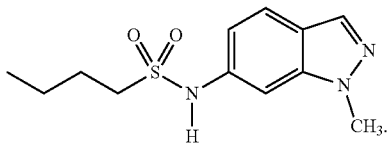 [SMILES: CCCCS(=O)(=O)Nc1ccc2cnn(C)c2c1]

The invention also provides a pharmaceutical composition comprising a compound of formula I or a pharmaceutically acceptable salt thereof, and a pharmaceutically acceptable excipient.

The invention also provides a method for treating a bacterial infection in an animal (e.g., a mammal such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of a bacterial infection.

The invention also provides the use of a compound of formula I or a pharmaceutically acceptable salt thereof to prepare a medicament for treating a bacterial infection in an animal (e.g. a mammal such as a human).

The invention also provides processes and intermediates disclosed herein that are useful for preparing a compound of formula I or a salt thereof.

BRIEF DESCRIPTION OF THE FIGURES

FIG. 1 Shows Table 1, DG167 active in laboratory and clinical strains of *M. tuberculosis* (Mtb).

FIG. 2 Shows Table 2, genotypic and drug-resistance profile (MIC in μM) of DG167 resistant Mtb isolates FIG. 3 Shows Table 3, structure-Activity Relationships for Representative Compounds.

FIGS. 4A-4D DG167 inhibits mycolic acid biosynthesis in vivo. (C-D) Normal-phase TLC analysis of MAMEs/FAMEs from wild-type *M. tuberculosis* (H37Rv) and the DG167-resistant *M. tuberculosis* (isolate: DRM167-32×2, Table 1). The cultures were treated with increasing concentrations of DG167 and inactive analog 5a-2. Total lipids were extracted, methyl esterified post $^{14}C$-acetate incorporation and resolved by TLCs (FIG. 4A) *M. tuberculosis* H37Rv (FIG. 4B). *M. tuberculosis* DRM167-32×2 isolate. (FIG. 4C) Densitometric analysis of MAMEs and FAMEs from panel A using ImageQuant (GE Healthcare) (FIG. 4D). Densitometric analysis of MAMEs and FAMEs from panel B. Equal counts (20,000 cpm) were loaded and the TLC was developed using hexane/ethyl acetate (19:1, v/v, 2 runs).

FIGS. 5A-5C DG167 synergizes with INH in vitro and in vivo. (FIG. 5A) In vitro killing curves for the *M. tuberculosis* strain H37Rv after incubation with given concentrations of DG167, INH, or a combination of these drugs. Killing activity was monitored by plating for CFUs; (FIG. 5B) Venn diagram showing differential gene expression from an RNAseq experiment upon treatment with 10×DG167, 10×INH or the drug combination; (FIG. 5C) In vivo efficacy of DG167 and INH alone and in combination in an acute model of *M. tuberculosis* infection in mice. The arrow indicates the day when treatment was started.

FIGS. 6A-6C Schematic representation of (FIG. 6A) $DG167_A$-$DG167_B$, and $DG167_A$-KasA interactions, (FIG. 6B) $DG167_A$-$DG167_B$, $DG167_B$-KasA, and $DG167_B$-KasA' interactions, and (FIG. 6C) KasA-PL interactions in PDB ID 4C72 chain A (Schiebel, J., et al., *J Biol Chem,* 2013, 288, 34190-34204). Molecules are labeled consistently throughout the figure—$DG167_A$ is depicted as green bonds, $DG167_B$ is depicted as magenta bonds, phospholipid (PL) is depicted as yellow bonds, and hydrogen bonds are depicted as dashed lines measured in Å. In panel A, the blue semicircles with radiating lines represent hydrophobic contacts mediated by KasA residues and $DG167_A$. In panel B, the blue semicircles with radiating lines represent hydrophobic contacts mediated by KasA residues and $DG167_B$, while orange semicircles with radiating lines represent hydrophobic contacts mediated by KasA' residues and $DG167_B$. In panel C, the blue semicircles with radiating lines represent hydrophobic contacts mediated by KasA residues and PL, while orange semicircles with radiating lines represent hydrophobic contacts mediated by KasA' residues and PL. PL-binding residues surrounded with a green, magenta, or red line identify residues from the KasA-DG167 structure that interact with $DG167_A$, $DG167_B$, or both, respectively. The schematic was produced with LIGPLOT (Wallace, A. C., et al., *Protein Eng,* 1995, 8, 127-134).

FIG. 7 Synthetic scheme. The N-methylation of commercially available 6-nitro-1H-indazole afforded a mixture of 1-methyl-6-nitro-1H-indazole and 2-methyl-6-nitro-1H-indazole. The chromatographically separable 1-methyl-6-nitro-1H-indazole was reduced and then the free amine was derivatized using four different methods depending on the desired functional group to generate the analytically pure compounds. The parent compound (DG167) was synthesized by treating 6-amino-1-methyl-1H-indazole with butane-1-sulfonyl chloride in the presence of pyridine. Reagents and conditions: (a) (i) NaH, DMF, 0° C., 30 min (ii) $R^1$, DMF, room temperature, 16 hours or $R^1I$ (1.2 eq), CuI (0.05 eq), $K_3PO_4$ (2eq), N,N-dimethylethylenediamine (0.1 eq), DMF, 110° C., 72 hours; (b) 10 wt % Pd/C, $HCOONH_4$, EtOH, room temperature, 4 hours; (c) $R^2SO_2Cl$, py, room temperature, 16 hours; (d) (i) NaH, DMF, 0° C., 30 min (ii) $CH_3I$, DMF, room temperature, 16 hours; (e) $R^2NCS/R^2CNO$, TEA, DCM, 40° C., 16 hours; (f) (i) 1,1' carbonyldiimidazole, DCM, 35° C., 4 hours; (ii) $R^2OH$, DCM, 35° C., 16 h; (g) $R^2COCl$, py, room temperature, 16 hours; (h) $LiAlH_4$, THF, 4 hours.

FIG. 8 Oral Bioavailability of DG167. DG167 was orally bioavailable and dotted line showed exposure in plasma above the MIC (104 ng/ml=0.39 μM). The mice dosing was either oral (PO 25 mg/kg) or intravenous (IV 5 mg/kg) in the following formulations and DG167 levels were measured in plasma using LC/MS. Each point was the average of three replicates. PO study in mice (25 mg/kg): 0.5% CMC/0.5% Tween 80; AUC [0-t]=8083.96 h*ng/mL; Bioavailability (%)=92.3; IV study in mice (5 mg/kg): 5% DMA/40% PEG300/55% D5W; AUC [0-t]=1751.25 h*ng/mL; t1/2=0.33 h.

FIG. 9 shows data for DG167 Tolerability Study with combined dosing of DG167 (100 mg/kg) and INH (25 mg/kg).

Figure 10:
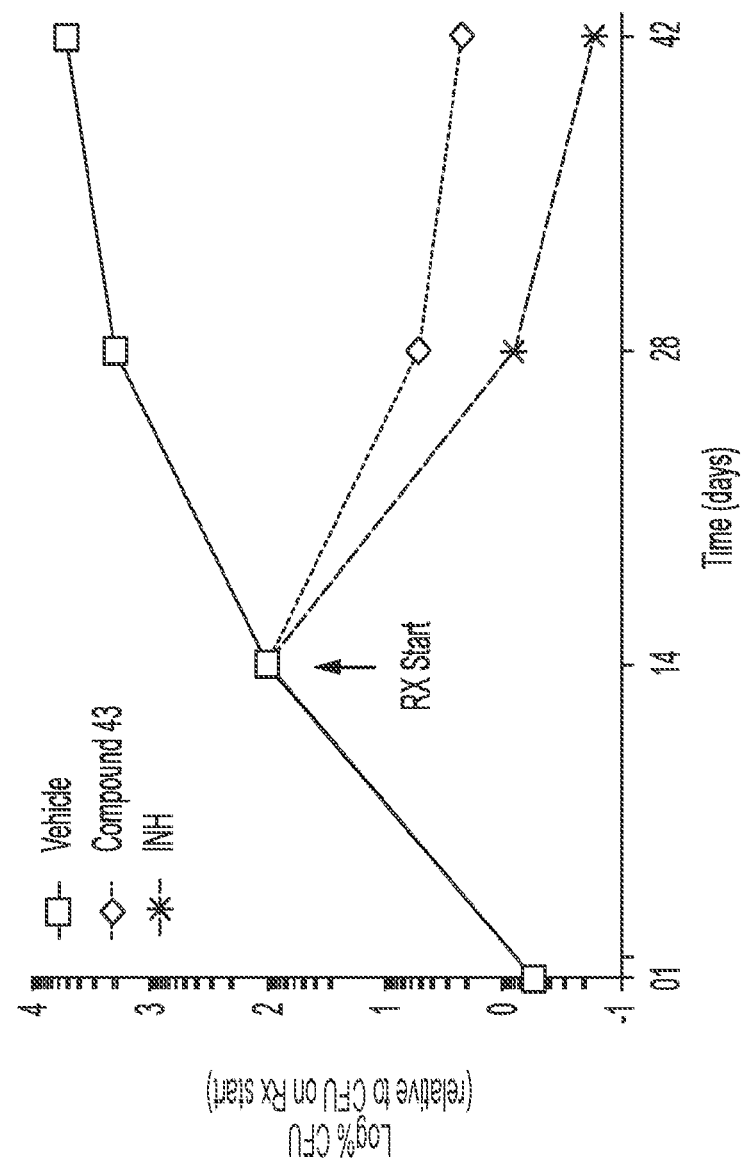

FIG. 10 shows the reduction of M. tuberculosis colony-forming units in the lungs of infected mice (PMID: 25421483) treated with compound 43 as compared to INH treatment and vehicle only.

Figure 12:
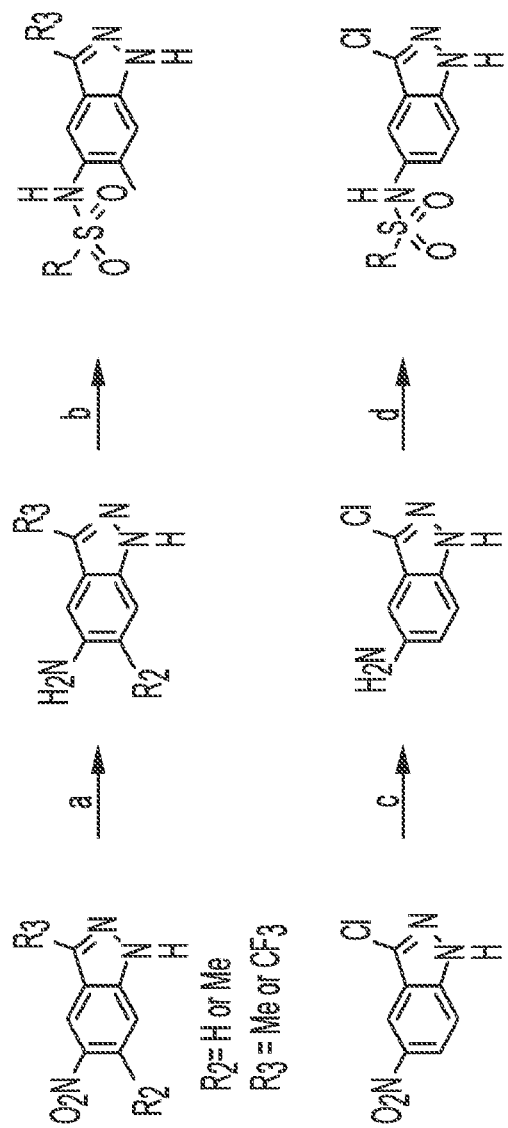
Figure 13A:
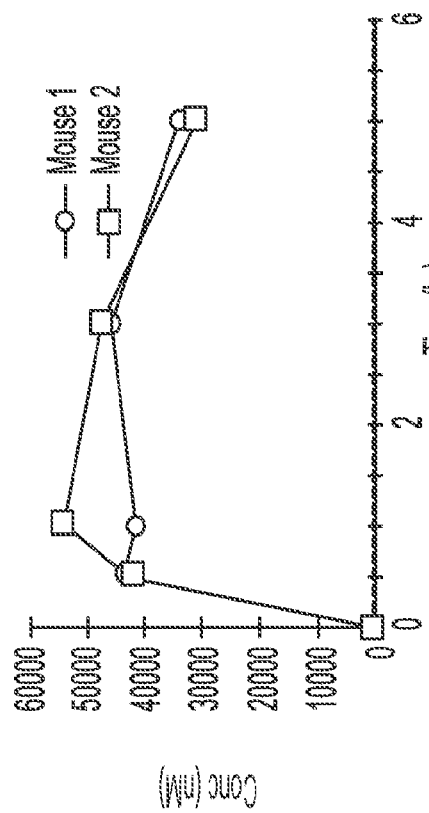
Figure 13B:
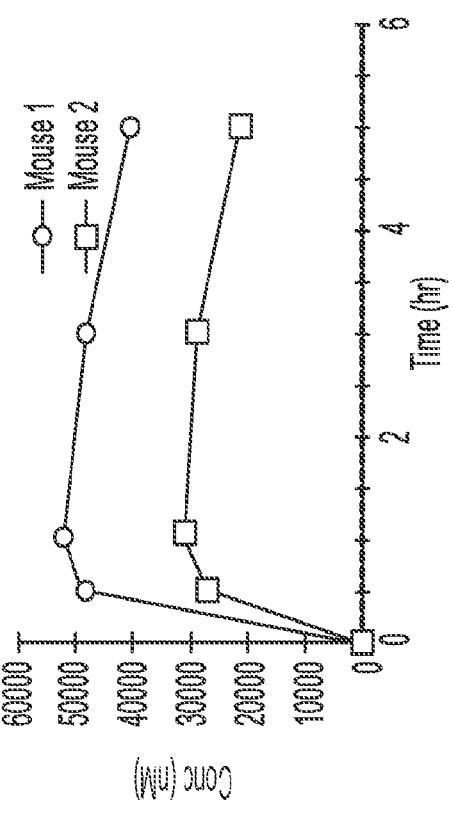
Figure 13C:
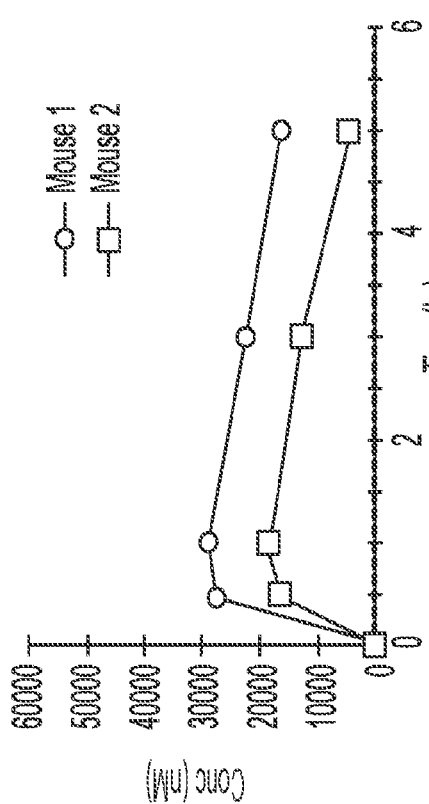
Figure 13D:
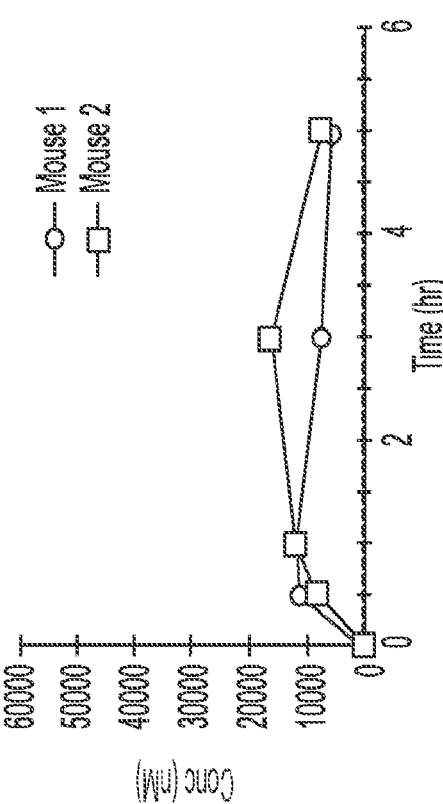

FIG. 11 shows the kinetic solubility and in vitro metabolic stability of the compounds of Examples 41, 42, 43, and 45. Published protocols were utilized to determine mouse and human liver microsomal stability (PMID: 26257441) and kinetic solubility (Kerns, E. H.; Di, L. Drug-like Properties: Concepts, Structure Design and Methods: from ADME to Toxicity Optimization; Elsevier: Amsterdam, 2008.) FIG. 12 illustrates the synthesis of representative compounds of the invention.

FIGS. 13A-13G show pharmacokinetic profiles of (FIG. 13A) Example 41, (FIG. 13B) Example 43, (FIG. 13C) Example 42, (FIG. 13D) Example 45, (FIG. 13E) Example 44, (FIG. 13F) Example 48, and (FIG. 13G) Example 46 in CD-1 female mice dosed at 25 mg/kg po. The dashed line in each plot represents the MIC of each compound. A published protocol was utilized for the mouse PK studies (PMID: 29311070).

Figure 14A:
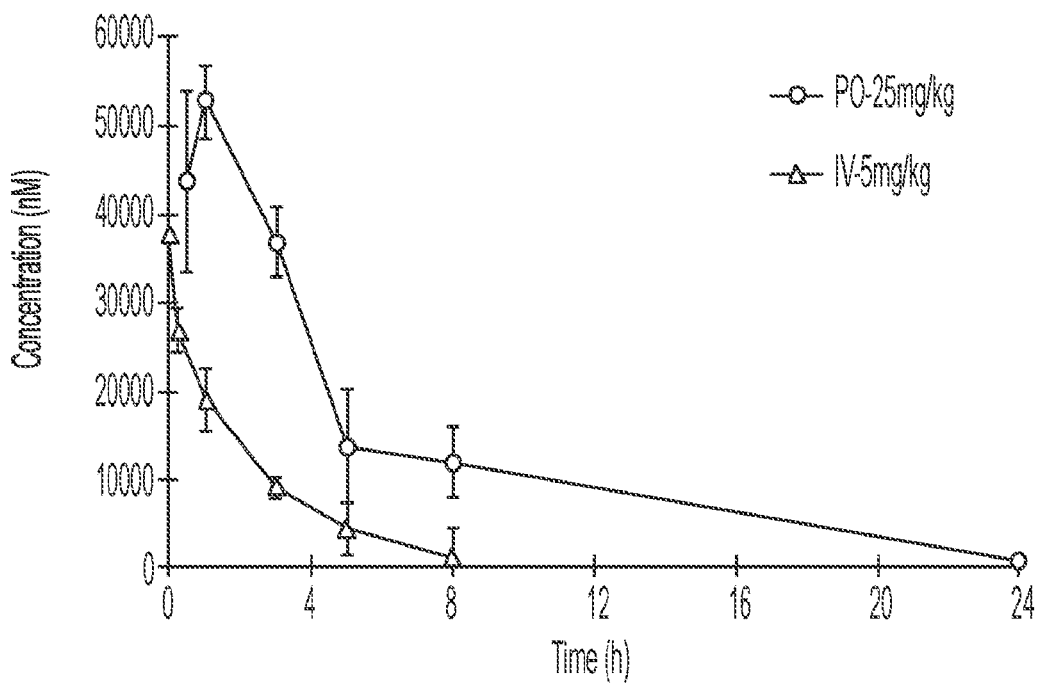
Figure 14B:
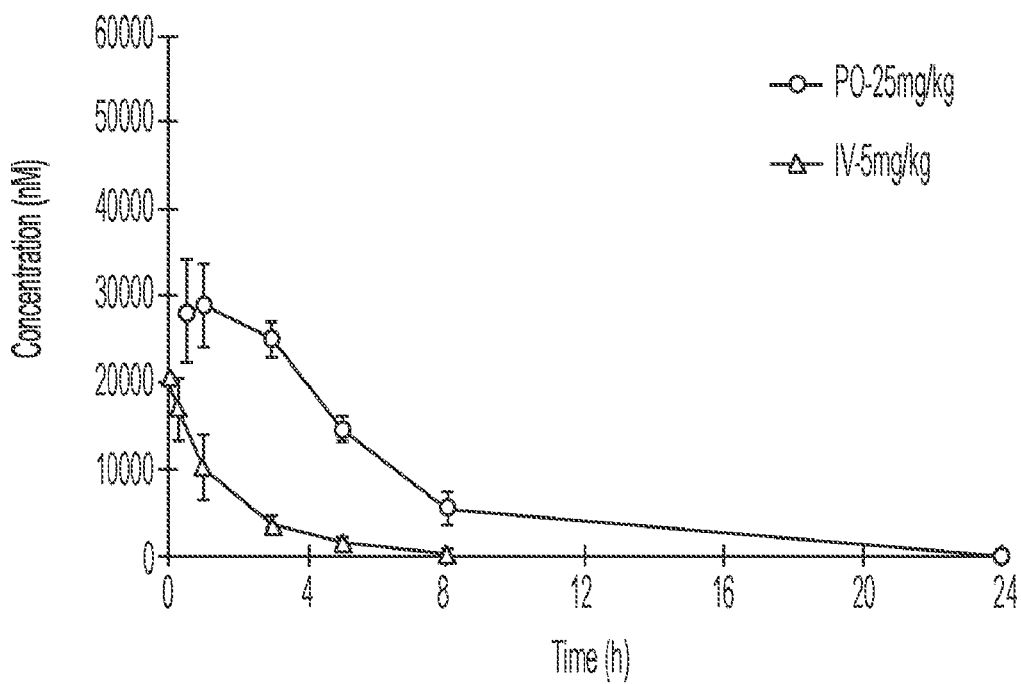

FIGS. 14A-14B show the pharmacokinetic profiles of (FIG. 14A) Example 43 and (FIG. 14B) Example 43 from a single dose of 5 mg/kg iv and 25 mg/kg po. A published protocol was utilized for the mouse PK studies (PMID: 29311070).

DETAILED DESCRIPTION

The following definitions are used, unless otherwise described: halo or halogen is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, tert-butyl, iso-butyl, sec-butyl, n-pentyl, n-hexyl, n-heptyl, n-octyl, and higher homologs and isomers.

The term "alkoxy" refers to an alkyl groups attached to the remainder of the molecule via an oxygen atom ("oxy").

The term "cycloalkyl" refers to a saturated or partially unsaturated (non-aromatic) all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocycles such as a bicyclic carbocycles (e.g., bicyclic carbocycles having about 3 to 15 carbon atoms, about 6 to 15 carbon atoms, or 6 to 12 carbon atoms such as bicyclo[3.1.0] hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein a wavy line "〰" that intersects a bond in a chemical structure indicates the point of attachment of the bond that the wavy bond intersects in the chemical structure to the remainder of a molecule.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$. When a compound is shown or named as containing a specific isotope, it is understood that the compound is enriched in that isotope above the natural abundance of that isotope. In one embodiment the compound may be enriched by at least 2-times the natural abundance of that isotope. In one embodiment the compound may be enriched by at least 10-times the natural abundance of that isotope. In one embodiment the compound may be enriched by at least 100-times the natural abundance of that isotope. In one embodiment the compound may be enriched by at least 1000-times the natural abundance of that isotope.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine) followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, (C$_1$-C$_8$)alkyl can be methyl, ethyl, propyl, isopropyl, butyl, iso-butyl, sec-butyl, pentyl, 3-pentyl, or hexyl; $(C_3\text{-}C_8)$cycloalkyl can be cyclopropyl, cyclobutyl, cyclopentyl, or cyclohexyl; $(C_1\text{-}C_8)$alkoxy can be methoxy, ethoxy, propoxy, isopropoxy, butoxy, iso-butoxy, sec-butoxy, pentoxy, 3-pentoxy, or hexyloxy; $(C_1\text{-}C_8)$alkanoyl can be acetyl, propanoyl or butanoyl; $(C_1\text{-}C_8)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2\text{-}C_8)$alkanoyloxy can be acetoxy, propanoyloxy, butanoyloxy, isobutanoyloxy, pentanoyloxy, or hexanoyloxy; and aryl can be phenyl, indenyl, or naphthyl.

In one embodiment $R^1$ is H.
In one embodiment $R^1$ is $(C_1\text{-}C_4)$alkyl.
In one embodiment $R^1$ is H, methyl, or $CD_3$.
In one embodiment $R^2$ is H.
In one embodiment $R^2$ is $(C_1\text{-}C_4)$alkyl.
In one embodiment $R^2$ is H or methyl.
In one embodiment $R^3$ is H and $R^4$ is $-N(R^a)SO_2R^c$.
In one embodiment $R^3$ is $-N(R^a)SO_2R^c$ and $R^4$ is H.
In one embodiment $R^3$ is H and $R^4$ is $-N(R^a)C(=S)N(R^a)R^c$.
In one embodiment $R^3$ is $-N(R^a)C(=S)N(R^a)R^c$ and $R^4$ is H.
In one embodiment each $R^a$ is H.
In one embodiment each $R^a$ is $(C_1\text{-}C_4)$alkyl.
In one embodiment each $R^a$ is methyl.
In one embodiment $R^c$ is $(C_2\text{-}C_6)$alkyl that is optionally substituted with one or more groups independently selected from the group consisting of halo and cyano.
In one embodiment $R^c$ is $(C_3\text{-}C_6)$alkyl that is optionally substituted with one or more groups independently selected from the group consisting of halo and cyano.
In one embodiment $R^c$ is $(C_3\text{-}C_5)$alkyl that is optionally substituted with one or more groups independently selected from the group consisting of halo and cyano.
In one embodiment $R^c$ is $(C_3\text{-}C_4)$alkyl that is optionally substituted with one or more groups independently selected from the group consisting of halo and cyano.
In one embodiment $R^c$ is butyl, 4-cyanobutyl, or cyclohexyl.

One embodiment provides a compound of formula (Ia):

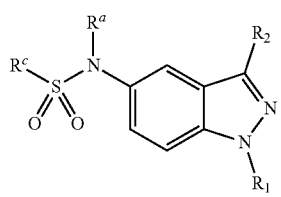

(Ia)

or a salt thereof.

One embodiment provides a compound of formula (Ib):

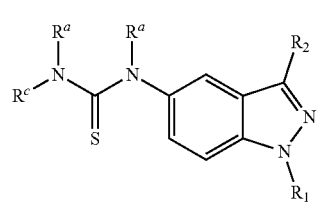

(Ib)

or a salt thereof.

One embodiment provides a compound of formula (Ic):

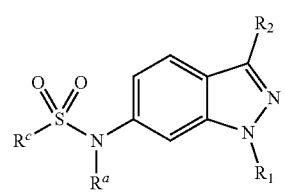

(Ic)

or a salt thereof.

One embodiment provides a compound of formula (Id):

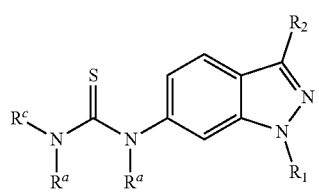

(Id)

or a salt thereof.

One embodiment provides a compound of formula (Ie):

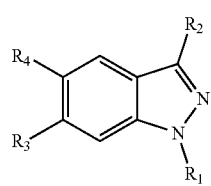

(Ie)

wherein $R^2$ is H, halo, or $(C_1\text{-}C_4)$alkyl or a salt thereof.

In one embodiment $R^1$ is H.
In one embodiment $R^1$ is methyl or $CD_3$.
In one embodiment $R^2$ is H.

One embodiment provides a compound selected from the group consisting of:

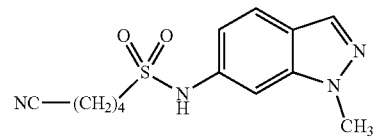

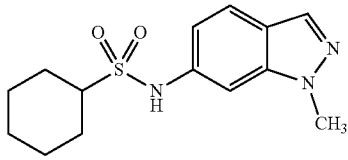

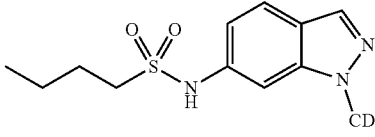

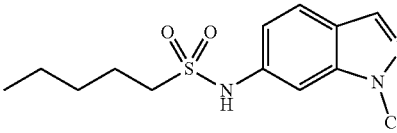

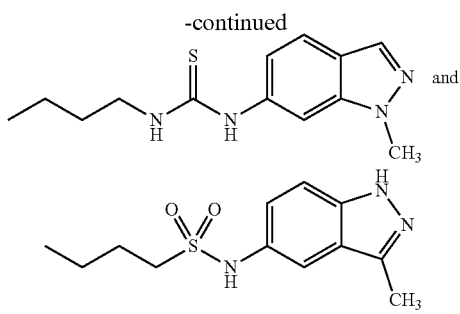

and or a salt thereof.

In one embodiment, $R^1$ is H, or $(C_1-C_4)$alkyl; $R^2$ is H, $(C_1-C_4)$alkyl, or halo; $R^3$ is H and $R^4$ is —N($R^a$)SO$_2R^c$ or —N($R^a$)C(=S)N($R^a$)R; or $R^3$ is —N($R^a$)SO$_2R^c$ or —N($R^a$)C(=S)N($R^a$)$R^c$ and $R^4$ is H; and each $R^a$ is independently H or $(C_1-C_4)$alkyl; and $R^c$ is $(C_3-C_6)$cycloalkyl, or $(C_2-C_6)$alkyl, wherein any $(C_3-C_6)$cycloalkyl and $(C_2-C_6)$alkyl is optionally substituted with one or more groups independently selected from the group consisting of halo, and cyano.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other antibacterial agents. Examples of such agents include isoniazid. Accordingly, in one embodiment the invention also provides a composition comprising a compound of formula I, or a pharmaceutically acceptable salt thereof, at least one other therapeutic agent, and a pharmaceutically acceptable excipient. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to treat a bacterial infection. The invention will now be illustrated by the following non-limiting Examples.

EXAMPLES

Example 1

Bacterial Strains, Culture Conditions, Primers and Plasmids.

M. tuberculosis strains were obtained from laboratory stocks. Clinical strains were obtained from a collection of clinical isolates for Research and Training in Tropical Diseases (TDR) established by UNICEF/UNDP/World Bank/WHO Special Programs. All M. tuberculosis strains were grown at 37° C. in Middlebrook medium 7H9 (Becton Dickinson, Sparks, Md.) enriched with 10% oleic acid-albumin-dextrose-catalase (OADC-Becton Dickinson) or 1×ADS (albumin (0.5 g/L)-dextrose(0.2 g/L)-sodium chloride (0.081 g/L)) and Tween 80 0.05% (wt/v) or tyloxapol (0.05% (wt/v) in liquid media. Middlebrook 7H10 agar (Becton Dickinson) supplemented with 10% OADC and 0.5% glycerol (v/v) was used to grow strains on solid media.

Reporter Screen for Cell-Wall Biosynthesis Inhibitors.

A total of 168 compounds previously identified as having anti-tubercular activity in a whole-cell screen by GlaxoSmithKline (Ballell, L., et al., Chem Med Chem, 2013, 8, 313-321) were tested for their ability to induce the iniBAC promoter (piniBAC). The promoter screen used a BCG strain (BCG$^S$(pG4697-6)) harboring the iniBAC promoter sequence fused to a lacZ reporter on an integrative plasmid (pG4697-6) (Alland, D., J Bacteriol, 2000, 182, 1802-1811). The BCG$^S$(pG4697-6) was grown to an OD600 of 0.2-0.3 and 90 μL was dispensed into each well of 96-deep well plates and then 10 μL of each compound (final concentration 10 μM) was added and incubated at 37° C. under shaking at 250 rpm. After incubation for 24 h, 100 μL of Lac Z buffer (60 mM $Na_2HPO_4·7H_2O$, 40 mM $NaH_2PO_4·H_2O$, 10 mM KCl, 1 mM $MgSO_4·7H_2O$, 50 mM β-mercaptoethanol) was added followed by addition of 5 μL of chloroform and 2 μL of 0.1% SDS and incubated for 5 minutes at room temperature (RT). Then, 40 μL of 4 mg/mL of LacZ substrate (2-nitrophenyl β-D-galactopyranoside, Sigma-Aldrich, St. Louis, Mo.) was added to each well and plates were incubated for 15 min. The reactions were terminated by adding 100 μL of 1 M aqueous sodium carbonate and absorbance was read at 420 nm. Fold induction was determined by $OD_{420}$ with compounds/$OD_{420}$ of vehicle (DMSO) controls. EMB and INH were used as positive controls.

Minimal Inhibitory Concentration (MIC) and Drug Interaction.

MIC assays in 96-well format were performed using the microdilution method (Kim, P., et al., J. Med. Chem., 2009, 52, 1329-1344). MICs were performed in 96 well plates using microdilution alamar blue (MABA) method. Briefly, the drugs were serially diluted in 50 μL of growth media (7H9-ADS) and supplemented 50 μL diluted cultures (1:1000) of M. tuberculosis grown to $OD_{595}$=0.2-0.3.

After incubation for 7 days at 37° C., AlamarBlue® Cell Viability Reagent (ThermoFischer Scientific, Grand Island, N.Y., USA) was added, the cultures were incubated for another 24 hours, and then the absorbance was read at 570 nm and normalized to 600 nM as per manufacturer's instruction. A checkerboard analysis (Reddy, V. M., et al., Antimicrobial Agents and Chemotherapy, 2010, 54, 2840-2846) was used to determine synergy and antagonism of the DG167 with INH. The fractional inhibitory concentration (FIC) was determined by dividing the MIC of the combination of drugs by the MIC of the drugs independently. Fractional inhibitory index (ΣFIC) was determined by adding the FICs of each drug tested. Activity of compounds were defined as synergistic if ΣFIC≤0.5, antagonistic if ΣFIC≥4.0, and additive if ΣFIC≥0.5 and <4.0 (Reddy et al., 2010).

Isolation of Resistant Mutants and Whole-Genome Sequencing.

The DG167-resistant Mtb mutants were isolated by plating 106-108 *M. tuberculosis* cells onto 7H10 plates containing 1×-32× of DG167. Plates were screened for DG167 resistant colonies after 3-4 weeks at 37° C. The genomic DNA was isolated (van Soolingen, D., et al., *Journal of Clinical Microbiology*, 1991, 29, 2578-2586) and subjected to whole-genome sequencing and single nucleotide polymorphism (SNP) analysis (Tahlan, K., et al., *Antimicrob Agents Chemother*, 2012, 56, 1797-1809).

Cloning and Purification of His-KasA.

*M. tuberculosis* kasA gene was PCR amplified using AccuPrime™ SuperMix (ThermoFischer Scientific) and primers (kasA-NheI: 5' CGAGGCTTGAGGCCGAGCTA-GCGTGAGTCAGCCTTC 3' and kasA-HindIII: 5' CCCGCGATGTCAAGCTTCAGTAACG 3'). The kasA amplicon was cloned between NheI HindIII restriction sites in pET28b plasmid inserting N-terminus $his_6$ tag. The kasA along with his tag was again PCR amplified using AccuPrime™ SuperMix and primers (kasA-SR113-Inf-Fp: 5' AAAGGGAGTCCATATGGGCAGCAGCCATCATCAT 3' and kasA-SR113-Inf-Fp: 5' GATAAGCTTCGAAT-TCTCAGTAACGCCCGAAGGC 3') and cloned in an acetamide inducible mycobacterial expression vector, pSR113 (Ryndak, M. B., et al., *J Bacteriol*, 2010, 192, 861-869) between NdeI-EcoRI using In-Fusion® HD Cloning kit (Takara Bio USA). The resultant construct pSR113-hisN-kasA was transformed into *Mycobacterium smegmatis* $mc^2$155. His-KasA was overexpressed in *M. smegmatis* grown in LB medium supplemented with 30 μg/mL kanamycin and 0.02% Tween-80 to an $OD_{600}$ of 0.6 at 37° C. Expression was induced with 0.02% w/v acetamide for 36 hours at 37° C. KasA was then purified using a modified version of a previously described protocol (Luckner, S. R., et al., *Structure*, 2009, 17, 1004-1013). Briefly, following expression the bacterial cells were collected via centrifugation at 5,000×g for 30 minutes and stored at −80° C. The cell pellet was resuspended in Buffer A [500 mM NaCl and 20 mM CHES (pH 9.5)] accompanied by 20 μg/mL DNase. Cells were then lysed via French Press at 15,000 psi and insoluble cell debris was separated via centrifugation at 25,000×g for 45 minutes. Lysate supernatant was applied to His-60 Ni Resin (Clontech) equilibrated in Buffer A, and KasA was eluted with Buffer A containing 200 mM imidazole. The eluted protein was then diluted to a final NaCl concentration of 50 mM using 20 mM CHES (pH 9.5) and loaded onto a MonoQ anion exchange column (GE Healthcare) equilibrated in 20 mM CHES (pH 9.5). KasA was eluted in a 50-1000 mM NaCl gradient of 20 mM CHES (pH 9.5) over 20 CV. Fractions containing KasA were pooled, concentrated using 10,000 molecular weight cutoff centrifugal filter units at 4,000×g, and further purified by passage over a Superdex-S200 16/70 (GE Healthcare) equilibrated in Buffer A. The final protein was then filtered through 0.22 μM Costar spin filters and stored at 4° C. All protein concentrations were determined by UV spectroscopy at 280 nm using molar extinction coefficients experimentally derived by the method of Gill and von Hippel (Gill, S. C., and von Hippel, P. H., *Anal Biochem*, 1989, 182, 319-326).

Crystallization and Data Collection.

KasA crystals were produced by the vapor diffusion method at 20° C. with 4.7 mg/mL of KasA in 2 μL hanging drops mixed 1:1 with mother liquor containing 200 mM NaCl with either 8% isopropanol and 1 mM Tris(2-carboxyethyl)phosphine hydrochloride (TCEP HCl) or 14% isopropanol and 2 mM TCEP HCl. Crystals from the condition containing 8% isopropanol were used to determine the structure of KasA-DG167 and Example 29 (trideuteriomethyl analog of DG167), while crystals from the condition containing 14% isopropanol were used to determine the structure of apo KasA. These conditions are similar but not identical to those previously used for crystallographic studies of KasA, which contained 10% isopropanol, 200 mM NaCl, 100 mM HEPES (7.5), and 10 mM TCEP HCl (Luckner, S. R., et al., *Structure*, 2009, 17, 1004-1013). KasA-DG167 crystals were obtained by moving apo KasA crystals from the hanging drops to 5 μL of soaking solutions containing 1 mM DG167, 8% isopropanol, 1 mM TCEP, 200 mM NaCl, and 1% DMSO for 1 h.

After 1 hour, the soaked crystal was placed in the same solution supplemented with 30% glycerol, immediately removed from the drop, and then flash-cooled in liquid nitrogen. Example 29 crystals were obtained in an identical manner by substituting the DG167 for 1 mM. Example 29. KasA-Example 41 crystals were grown in a similar manner with the following modification: the 2 μL hanging drops contained 1 μL of mother liquor and 1 μL of purified 110 μM KasA and 1 mM Example 41. The KasA-Example 41 crystals selected for data collection grew over the course of seven days in 200 mM NaCl, 2 mM TCEP HCl, and 4% isopropanol. These crystals were cryo-protected in their crystallization condition supplemented with 22% glycerol and 1 mM Example 41.

X-ray diffraction data were collected using single crystals mounted in nylon loops that were then flash-cooled in liquid nitrogen before data collection in a stream of dry $N_2$ at 100 K. ata sets for apo KasA, KasA-DG167, and Example 29 were collected at the Stanford Synchrotron Radiation Lightsource (SSRL) beamline 14-1 at 1.1808 Å with a MARmosaic 325 CCD detector. The KasA-5g data set was collected on beamline 9-2 at 0.88557 Å with a Dectris Pilatus 6M detector. X-ray data were processed using HKL2000 (Otwinowski, Z., and Minor, W. *Methods Enzymol*, 1997, 276, 307-326). Crystallographic phases for apo KasA were determined by molecular replacement using Phaser (McCoy, A. J., et al., *J Appl Crystallogr*, 2007, 40, 658-674) and the previously determined structure of apo KasA (PDB Code: 2WGD) as a search model (Luckner, S. R., et al., *Structure*, 2009, 17, 1004-1013). Crystallographic phases for KasA-DG167, Example 29, and KasA-Example 41 were determined by molecular replacement using Phaser (McCoy, A. J., et al., *J Appl Crystallogr*, 2007, 40, 658-674) and the previously determined structure of KasA bound to TLM5 (PDB Code: 4C6U) (Schiebel, J., et al., *J Biol Chem*, 2013, 288, 34190-34204). Models were generated using iterative cycles of model building in Coot (Emsley, P., et al., *Acta Crystallogr D Biol Crystallogr*, 2010, 66, 486-501) and refinement in phenix.refine (Adams et al., 2010). Initial refinement included simulated annealing as well as rigid body, individual atomic coordinate, and individual B-factor refinement. Later rounds of refinement employed individual atomic coordinate, individual B-factor, and TLS refinement. TLS groups were selected using the TLSMD server (Painter and Merritt, 2006). During the final rounds of refinement, the stereochemistry and ADP weights were optimized. DG167, Example 29, and water molecules were included only after the KasA models were complete. Insufficient electron density was observed for the following residues in flexible regions of the structures, and they were omitted from the model: apo KasA 1-25; KasA-DG167 1-25; Example 29 1-25. One sodium atom was built into clear electron density during the final stages of refinement. Ramachandran statistics were calculated in Molprobity (Lovell et al., 2003). Molecular graphics were produced with PyMOL (Delano, W. L. *The PyMOL Molecular Graphics System,* 2002).

Microscale Thermophoresis Binding Assays.

Prior to labeling, His-KasA was diluted from 100 μM in Buffer A to 200 nM in Buffer B (10 mM HEPES, 150 mM NaCl, pH 7.4). The diluted His-KasA was labeled using the RED-tris-NTA His-Tag Labeling kit (NanoTemper Technologies). 50 nM working stocks of labeled protein were made consisting of Buffer B supplemented with 0.1% Pluronic F-127. Threefold titrations of Example 1 and DG167 in DMSO were made, transferred by Labcyte 555 ECHO instrument into separate 384-well polypropylene plates, and incubated with 50 nM working stock solutions of labeled protein in the dark for 30 min at room temperature. After incubation, the samples were transferred into Premium Coated Capillaries and read in a Monolith NT. 115 Nano-BLUE/RED Instrument at room temperature using 60% LED and 60% MST power for DG167, and 60% LED and 40% MST power for Example 1. Binding affinities were calculated using the Thermophoresis with T Jump Evaluation strategy from a minimum of three experiments.

Analysis of Mycolic Acids.

The MAMEs and FAMEs (Slayden, R. A., and Barry, C. E., $3^{rd}$, *Molecular Medicine,* 2001, 54, 229-245) were analyzed as described previously. The compounds were added to 5 mL of *M. tuberculosis* cultures (OD595 of ~0.3-0.4), incubated at 37° C. for 2 hours and 1 μCi/mL of 14C-acetate (56 mCi/mmol) was added to each culture, followed by incubation at 37° C. for another 4 hours. The 14C-labeled cells were pelleted by centrifugation, resuspended in 2 mL of tetra-n-butylammonium hydroxide (TBAH) and incubated overnight at 100° C. to hydrolyze cell-wall bound lipids. The fatty acids were esterified by adding 4 mL CH2Cl2, 300 μL iodomethane, and 2 mL distilled water (dH2O) and mixing at room temperature for 1 hour, the phases were separated by centrifugation, the upper aqueous phase was discarded and the lower organic phase was washed twice with dH2O, dried and resuspended in 3 mL of diethyl ether. Insoluble material was removed by centrifugation, the organic phase was dried and lipids were resuspended in 200 μL $CH_2Cl_2$. Equal counts (20,000 cpm) were loaded on a silica gel 60 F254 thin-layer chromatography (TLC) plate and resolved using hexane/ethyl acetate (19:1, v/v, 2 runs). The FAMEs and MAMEs were detected by phosphorimaging.

Killing Studies Using CFU Measurements.

*M. tuberculosis* cells (~107 CFU/mL) were treated with compounds, incubated at 37° C. under shaking, the samples were drawn at specific time points and total viable counts determined by dilution plating on 7H10-OADC-agar plates and counting colony forming units after 4-week incubation at 37° C.

RNAseq Analysis.

*M. tuberculosis* H37Rv was grown to OD595 to ~0.4 tissue culture flasks (50 mL each) and pooled. The cultures (10 mL) were redistributed into flasks containing each compound or compound combination or vehicle (DMSO) control. The final concentration of DMSO was kept constant in each flask. After 4 h incubation at 37° C. with shaking, the cultures were harvested by centrifugation and total RNA was extracted using TRIzol® LS reagent (ThermoFisher Scientific) and bead beating followed by extraction with the RNeasy® Mini Kit (Qiagen) as described (Malherbe et al., 2016). The integrity and purity of RNA was determined by bioanalyzer (2100, Agilent), rRNA was removed, and the cDNA library was prepared. The sequencing of the cDNA libraries was performed on the Illumina NextSeq 500 platform (Illumina, San Diego, Calif.) using the high output 1×75 cycles configuration. CLC Genomics Workbench 9.0.1 version (http://www.clcbio.com/products/clc-genomics-workbench/; Qiagen) was utilized for RNA-seq analysis. De-multiplexed fastq files from RNA-Seq libraries were imported into the CLC software. Bases with low quality were trimmed and reads were mapped to the reference genome, *Mycobacterium tuberculosis* H37Rv (NCBI Reference Sequence: NC_000962.3). The aligned reads were obtained using the RNA-Seq Analysis Tool of CLC Genomics Workbench. RPKM values were calculated for each gene to quantify absolute expression. Statistical analysis of differentially expressed genes was carried out with the Empirical analysis of Digital Gene Expression data tool in CLC Genomic Workbench. Replicates were averaged, and genes with FDR adjusted p value<0.05 and fold change of an absolute value>2.0 were identified.

Mouse Pharmacokinetic Studies.

All animal experiments were conducted in compliance with and approved by the Institutional Animal Care and Use Committee of the New Jersey Medical School, Rutgers University. Female BALB/c mice were weighed (23-29 g) and treated via oral gavage with a single dose of DG167 (100 mg/kg) formulated in 0.5% CMC/0.5% Tween 80. Sequential bleeds were collected at 0.25, 0.5, 1, 3, 5 and 8 h post-dose via tail snip method. Blood (50 μL) was collected in capillary microvette EDTA blood tubes and kept on ice prior to centrifugation at 1,500 g for 5 minutes. The supernatant (plasma) was transferred into a 96-well plate and stored at −80° C. In a dose escalation study, mice were dosed with 50, 100, 250 or 500 mg/kg DG167, and blood was similarly sampled and processed.

Quantitative Analysis.

DG167 levels in plasma were measured by LC-MS/MS in electrospray positive-ionization mode (ESI+) on a Sciex Qtrap 4000 triple-quadrupole mass combined with an Agilent 1260 HPLC using Analyst software. Chromatography was performed with an Agilent Zorbax SB-C8 column (2.1×30 mm; particle size, 3.5 μm) using a reverse phase gradient elution. 0.1% formic acid in Milli-Q deionized water was used for the aqueous mobile phase and 0.1% formic acid in acetonitrile (ACN) for the organic mobile phase. Multiple-reaction monitoring (MRM) of parent/daughter transitions in electrospray positive-ionization mode (ESI+) was used to quantify DG167. A DMSO stock of DG167 was serial diluted in blank K2EDTA plasma (Bioreclammation) to create standard curves and quality control samples. DG167 was extracted by combining 20 μL of spiked plasma or study samples and 200 μL of acetonitrile/methanol (50/50) protein precipitation solvent containing 20 ng/mL verapamil internal standard (IS). Extracts were vortexed for 5 minutes and centrifuged at 4000 RPM for 5 minutes. The supernatants were analyzed by LC-MS. Verapamil IS was sourced from Sigma-Aldrich. The following MRM transitions were used for DG167 (268.1/146) and verapamil (455.4/165.2). Sample analysis was accepted if the concentrations of the quality control samples were within 20% of the nominal concentration.

Drug Tolerability.

Five mice were dosed orally daily for 5 days with DG167 (100 mg/kg) formulated in 0.5% CMC/0.5% Tween 80 and INH (25 mg/kg) in water. Prior to dosing, DG167 and INH were mixed (1:1) and vortexed. The mice were weighed and observed daily. Their behavior, drinking and feeding patterns, and feces were monitored and recorded. Upon necropsy, liver, gall bladder, kidney and spleen pathology were observed as well.

Mouse Efficacy.

Nine week-old female BALB/c mice (weight range 18-20 g) were infected with an inoculum of *M. tuberculosis* H37Rv in 5 mL of PBS (3×106 CFU/mL) using a Glas-Col whole body aerosol unit. This resulted in lung implantation of 1.09 log 10 CFU per mouse. Groups of 5 mice were sacrificed by cervical dislocation at the start of treatment (2-week post-infection), and after receiving DG167 at 100 mg/kg, INH at 25 mg/kg, the combination (DG167 at 100 mg/kg+INH at 25 mg/kg) or the vehicle only for 3 days, 1 week, or 2 weeks daily. Whole lungs were homogenized in 5 mL of PBS containing 0.05% Tween 80. CFU were determined by plating serial dilutions of homogenates onto Middlebrook 7H11 agar with OADC. Colonies were counted after at least 21 days of incubation at 37° C.

Synthesis of DG167 and its Analogs.

All reagents were purchased from commercial suppliers and used without further purification unless noted otherwise. All chemical reactions occurring solely in an organic solvent were carried out under an inert atmosphere of argon or nitrogen. Analytical TLC was performed with Merck silica gel 60 F254 plates. Silica gel column chromatography was conducted with Teledyne Isco CombiFlash Companion or Rf+ systems. $^1$H NMR spectra were acquired on Bruker 500 MHz instruments and are listed in parts per million downfield from TMS. LC-MS was performed on an Agilent 1260 HPLC coupled to an Agilent 6120 MS. All synthesized compounds were at least 95% pure as judged by their HPLC trace at 250 nm and were characterized by the expected parent ion(s) in the MS.

Figure 7:
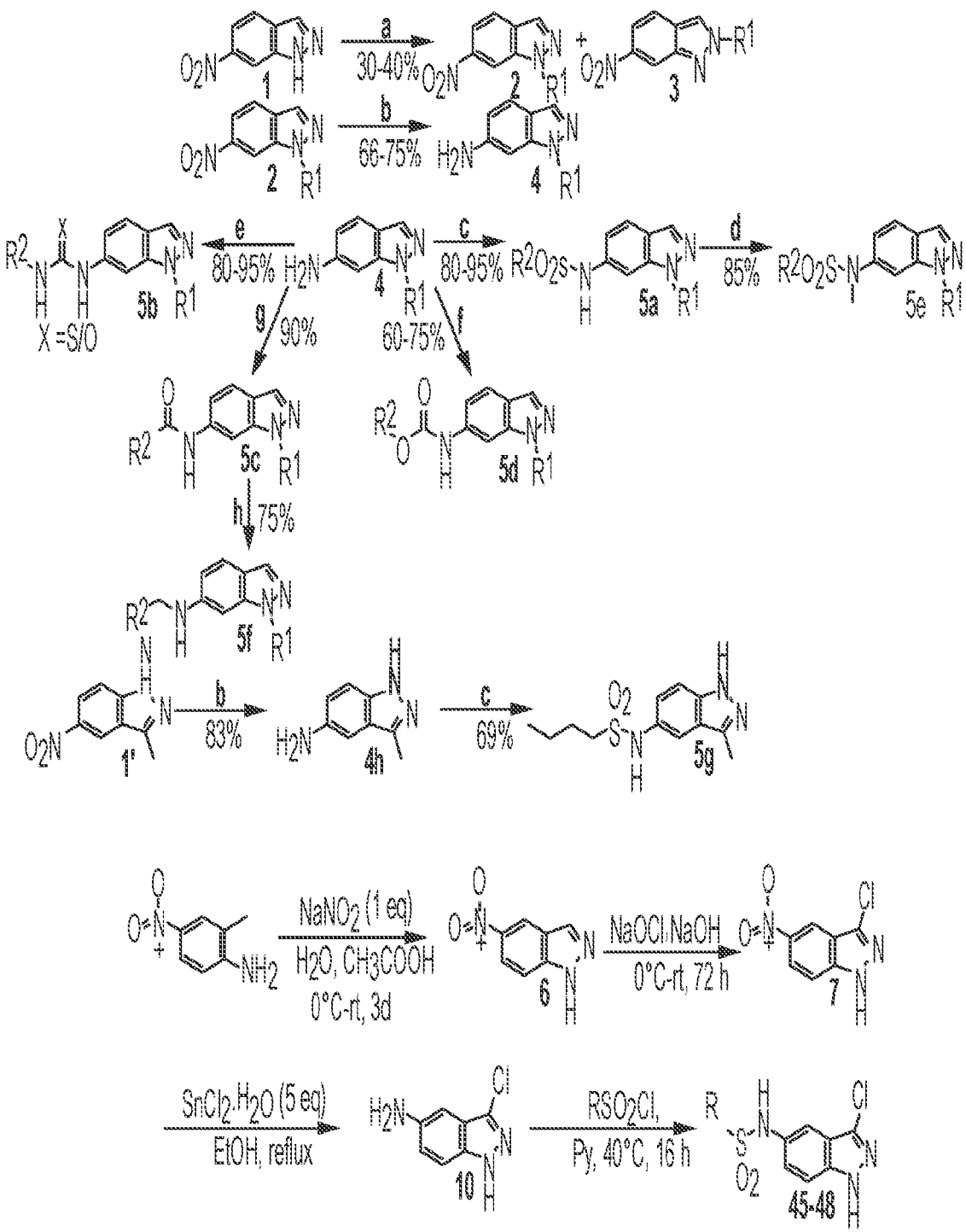

Synthesis of 1-methyl-6-nitro-1H-indazole (2a, FIG. 7)

To a vigorously stirring, ice cold solution of 6-nitro-1H-indazole (4.14 g, 25.4 mmol) in dimethylformamide (100 mL), NaH (2.03 g, 50.7 mmol) was added in four portions. The reaction mixture was maintained at 0° C. for 30 minutes. Iodomethane (1.74 mL, 27.9 mmol) was added dropwise to the reaction mixture and the reaction was stirred for 16 hours at room temperature. The reaction mixture was quenched with water and diluted with ethyl acetate. The reaction mixture was transferred to a separatory funnel, washed with water three times and dried over anhydrous magnesium sulfate. The reaction mixture was concentrated on a rotary evaporator and 1-methyl-6-nitro-1H-indazole was separated from 2-methyl-6-nitro-2H-indazole by flash chromatography on silica using ethyl acetate as eluent to afford the product as a yellow solid (2.54 g, 56.4% yield): 1H NMR (600 MHz, DMSO) δ 8.73 (s, 1H), 8.29 (s, 1H), 8.01 (d, J=8.79 Hz, 1H), 7.95 (dd, J=1.47, 8.79 Hz, 1H), 4.19 (s, 3H).

Using a procedure similar to that described for Compound 2a, 1-ethyl-6-nitro-1H-indazole (2b, FIG. 7), 6-nitro-1-propyl-1H-indazole (2c, FIG. 7), 1-benzyl-6-nitro-1H-indazole (2d, FIG. 7), and 1-(methyl-d3)-6-nitro-1H-indazole (2e, FIG. 7) were prepared.

Synthesis of 1-isopropyl-6-nitro-1H-indazole (2f, FIG. 7)

A solution of 6-nitro-1H-indazole (378 mg, 2.32 mmol), isopropyl iodide (277.5 µL, 2.780 mmol), copper (I) iodide (22 mg, 0.12 mmol), potassium phosphate (985 mg, 4.64 mmol), N,N-dimethylethylenediamine (25.3 µL, 0.232 mmol) in dimethylformamide (1.2 mL) was stirred at 110° C. for 72 h. After completion of the reaction, the reaction mixture was filtered over Celite and the filtrate was diluted with ethyl acetate, transferred to a separatory funnel, washed with water three times and dried over anhydrous magnesium sulfate. The reaction mixture was concentrated on a rotary evaporator and 1-isopropyl-6-nitro-1H-indazole was separated from 2-isopropyl-6-nitro-2H-indazole by flash chromatography on silica using ethyl acetate as eluent to afford the product as a yellow solid (199 mg, 56.4% yield): 1H NMR (500 MHz, CDCl3) δ 7.97 (s, 1H), 7.67 (d, J=8.54 Hz, 1H), 7.43 (s, 1H), 6.86 (dd, J=1.8, 8.5 Hz, 1H), 6.63 (s, 1H), 4.80 (td, J=6.6, 13.3 Hz, 1H), 3.03-3.20 (m, 2H), 1.72-1.92 (m, 2H), 1.58 (d, J=6.4 Hz, 6+1 H from H2O), 1.31-1.51 (m, 2H), 0.90 (t, J=7.3 Hz, 3H).

Using a procedure similar to that described for Compound 2f, 1-phenyl-6-nitro-1H-indazole (2g, FIG. 7) was prepared.

Synthesis of 1-methyl-1H-indazol-6-amine (4a)

To a solution of 1-methyl-6-nitro-1H indazole (2a) (2.5 g, 14.2 mmol) in ethanol (150 mL) was added ammonium formate (7 g) and 10 wt % Pd/C (1 g). The mixture maintained under nitrogen was stirred at room temperature for 3 hours. After completion of reaction, the Pd/C catalyst and excess ammonium formate were removed via filtration of the crude reaction mixture through a pad of Celite. The filtrate was concentrated on the rotary evaporator to remove ethanol. The crude material was purified by flash chromatography on silica gel to obtain 1-methyl-1H-indazol-6-amine (4a) as a light pink solid (1.61 g, 77% yield): $^1$H NMR (500 MHz, CDCl3) δ 7.80 (s, 1H), 7.48 (d, J=8.54 Hz, 1H), 6.57 (d, J=8.54 Hz, 1H), 6.53 (s, 1H), 3.94 (s, 3H), 3.88 (br s, 2H).

Using a procedure similar to that described for Compound 4a, 1-ethyl-1H-indazol-6-amine (4b), 1-propyl-1H-indazol-6-amine (4c), 1-benzyl-1H-indazol-6-amine (4d), 1-(methyl-d3)-1Hindazol-6-amine (4e), 1-isoproyl-1H-indazol-6-amine (4f), 1-phenyl-1H-indazol-6-amine (4g) and 3-methyl-5-nitro-1H-indazole (4h) were prepared.

Synthesis of N-(1-methyl-1H-indazol-6-yl)butane-1-sulfonamide (DG167 (5a-1))

To a solution of 1-methyl-1H-indazol-6-amine (464 mg, 3.15 mmol) in pyridine (20 mL) was added n-butyl sulfonyl chloride (450 µL, 3.47 mmol) and the reaction was stirred at room temperature for 16 hours. After completion of the reaction, the reaction mixture was diluted with ethyl acetate and transferred to a separatory funnel. The organic layer was washed with saturated aqueous sodium bicarbonate solution, followed by water, and brine. The organic layer was dried over anhydrous magnesium sulfate, filtered and concentrated. The crude product was purified by flash chromatography on silica gel (gradient: 30-70% ethyl acetate/hexanes) to obtain the product as a white solid (700 mg, 83% yield): $^1$H NMR (500 MHz, CDCl3) δ 7.94 (s, 1H), 7.67 (d, J=8.5 Hz, 1H), 7.39 (s, 1H), 7.11 (br. s., 1H), 6.91 (dd, J=1.8, 8.5 Hz, 1H), 4.05 (s, 3H), 3.17-3.09 (m, 2H), 1.89-1.77 (m, 2H), 1.45-1.35 (m, 2H), 0.88 (t, J=7.5 Hz, 3H).

Using a procedure similar to that described for the synthesis of the DG167(5a-1), the following Example compounds 1-31 were prepared.

Example 1
N-(1H-indazol-6-yl)butane-1-sulfonamide $^1$H NMR (500 MHz, CDCl3) δ 8.06 (s, 1H), 7.49 (d, J=8.54 Hz, 1H), 6.70 (dd, J=1.83, 8.54 Hz, 1H), 4.07 (br s, 1H), 3.31-3.41 (m, 2H), 1.66 (td, J=7.67, 15.49 Hz, 2H), 1.36 (qd, J=7.44, 14.92 Hz, 2H), 0.86 (t, J=7.32 Hz, 3H).

Example 2
N-(1-ethyl-1H-indazol-6-yl)butane-1-sulfonamide $^1$H NMR (500 MHz, CDCl3) δ 7.90-8.00 (m, 1H), 7.67 (d, J=8.5 Hz, 1H), 7.41 (s, 1H), 6.87 (d, J=8.5 Hz, 1H), 6.77 (s, 1H), 4.41 (q, J=7.3 Hz, 2H), 3.07-3.18 (m, 2H), 1.82 (quin, J=7.7 Hz, 2H), 1.51 (t, J=7.3 Hz, 3H), 1.41 (qd, J=7.3, 14.9 Hz, 2H), 0.89 (t, J=7.3 Hz, 3H).

Example 3
N-(1-propyl-1H-indazol-6-yl)butane-1-sulfonamide $^1$H NMR (500 MHz, CDCl3) δ 7.95 (s, 1H), 7.67 (d, J=8.54 Hz, 1H), 7.40 (s, 1H), 6.85-6.96 (m, 2H), 4.31 (t, J=7.02 Hz, 2H), 3.06-3.16 (m, 2H), 1.89-1.99 (m, 2H), 1.76-1.87 (m, 2H), 1.34-1.45 (m, 2H), 0.82-0.96 (m, 6H).

Example 4 N-(1-isoproply-1H-indazol-6-yl)butane-1-sulfonamide $^1$H NMR (500 MHz, CDCl3) δ 7.97 (s, 1H), 7.67 (d, J=8.54 Hz, 1H), 7.43 (s, 1H), 6.86 (dd, J=1.83, 8.54 Hz, 1H), 6.63 (s, 1H), 4.80 (td, J=6.60, 13.35 Hz, 1H), 3.03-3.20 (m, 2H), 1.72-1.92 (m, 2H), 1.58 (d, J=6.41 Hz, 6H+1H from H2O), 1.31-1.51 (m, 2H), 0.90 (t, J=7.32 Hz, 3H).

Example 5
N-(1-phenyl-1H-indazol-6-yl)butane-1-sulfonamide $^1$H NMR (500 MHz, CDCl3) δ 8.17 (s, 1H), 7.75 (d, J=8.55 Hz, 1H), 7.65-7.73 (m, 3H), 7.55 (t, J=7.93 Hz, 2H), 7.33-7.42 (m, 1H), 7.02 (dd, J=1.68, 8.70 Hz, 1H), 6.70 (s, 1H), 3.06-3.17 (m, 2H), 1.76-1.87 (m, 2H), 1.34-1.45 (m, 2H), 0.89 (t, J=7.32 Hz, 3H).

Example 6
N-(1-benzyl-1H-indazol-6-yl)butane-1-sulfonamide $^1$H NMR (500 MHz, CDCl3) δ 8.00 (s, 1H), 7.67 (d, J=8.54 Hz, 1H), 7.14-7.43 (m, 5H), 6.87 (d, J=8.54 Hz, 1H), 6.60 (s, 1H), 5.57 (s, 2H), 2.92-3.11 (m, 2H), 1.74 (t, J=7.63 Hz, 2H), 1.28-1.43 (m, 2H), 0.85 (t, J=7.32 Hz, 3H).

Example 7
N-(1-methyl-1H-indazol-6-yl)methanesulfonamide $^1$H NMR (500 MHz, CD3OD) δ 7.94 (s, 1H), 7.70 (d, J=8.5 Hz, 1H), 7.41 (s, 1H), 7.03 (d, J=8.5 Hz, 1H), 4.02 (s, 3H), 3.00 (s, 3H).

Example 8
N-(1-methyl-1H-indazol-6-yl)ethanesulfonamide $^1$H NMR (500 MHz, CDCl3) δ 7.94 (br s, 1H), 7.67 (d, J=7.93 Hz, 1H), 7.39 (br s, 1H), 6.96 (br s, 1H), 6.91 (d, J=7.63 Hz, 1H), 4.05 (br s, 3H), 3.04-3.27 (m, 2H), 1.29-1.47 (m, 3H).

Example 9
N-(1-methyl-1H-indazol-6-yl)propane-1-sulfonamide $^1$H NMR (500 MHz, CDCl3) δ 7.94 (s, 1H), 7.67 (d, J=8.5 Hz, 1H), 7.39 (s, 1H), 6.86 (d, J=8.5 Hz, 1H), 6.61 (s, 1H), 4.06 (s, 3H), 3.06-3.15 (m, 2H), 1.88 (qd, J=7.5, 15.3 Hz, 2H), 1.02 (t, J=7.3 Hz, 3H).

Example 10
N-(1-methyl-1H-indazol-6-yl)propane-2-sulfonamide $^1$H NMR (500 MHz, Acetone) δ 8.75 (br s, 1H), 7.90 (s, 1H), 7.70 (d, J=8.54 Hz, 1H), 7.51 (s, 1H), 7.16 (dd, J=1.68, 8.70 Hz, 1H), 4.01 (s, 3H), 3.37 (td, J=6.75, 13.66 Hz, 1H), 1.33 (d, J=7.02 Hz, 6H).

Example 11
N-(1-methyl-1H-indazol-6-yl)pentane-1-sulfonamide $^1$H NMR (500 MHz, CDCl3) δ 7.94 (s, 1H), 7.67 (d, J=8.5 Hz, 1H), 7.39 (s, 1H), 6.88 (d, J=8.5 Hz, 1H), 6.77 (br s, 1H), 4.06 (s, 3H), 3.08-3.15 (m, 2H), 1.84 (quint, J=7.7 Hz, 2H), 1.23-1.40 (m, 4H), 0.86 (t, J=7.2 Hz, 3H).

Example 12
N-(1-methyl-1H-indazol-6-yl)hexane-1-sulfonamide $^1$H NMR (500 MHz, CDCl3) δ 7.95 (s, 1H), 7.67 (d, J=8.54 Hz, 1H), 7.39 (s, 1H), 6.88 (d, J=8.24 Hz, 1H), 6.81 (br s, 1H), 4.06 (s, 3H), 3.06-3.16 (m, 2H), 1.78-1.89 (m, 2H), 1.31-1.42 (m, 2H), 1.24 (br s, 2H+ grease), 0.81-0.87 (m, 3H).

Example 13 4-cyano-N-(1-methyl-1H-indazol-6-yl)butane-1-sulfonamide $^1$H NMR (500 MHz, CDCl3) δ 7.95 (s, 1H), 7.69 (d, J=8.5 Hz, 1H), 7.39 (s, 1H), 6.91 (d, J=8.2 Hz, 1H), 6.80 (s, 1H), 4.06 (s, 3H), 3.17 (t, J=7.3 Hz, 2H), 2.38 (t, J=6.9 Hz, 2H), 2.02 (quin, J=7.5 Hz, 2H), 1.75-1.86 (m, 2H).

Example 14 4-methoxy-N-(1-methyl-1H-indazol-6-yl)butane-1-sulfonamide $^1$H NMR (500 MHz, CDCl3) δ 7.94 (s, 1H), 7.67 (d, J=8.5 Hz, 1H), 7.39 (s, 1H), 6.88 (d, J=8.2 Hz, 1H), 6.84 (br s, 1H), 4.06 (s, 3H), 3.34 (t, J=5.5 Hz, 2H), 3.26 (s, 3H), 3.17 (t, J=7.5 Hz, 2H), 1.94 (quin, J=7.4 Hz, 2H), 1.59-1.68 (m, 2H).

Example 15 5-methoxy-3-methyl-N-(1-methyl-1H-indazol-6-yl)pentane-1-sulfonamide $^1$H NMR (500 MHz, CDCl3) δ 7.94 (s, 1H), 7.66 (d, J=8.54 Hz, 1H), 7.39 (s, 1H), 7.19 (br s, 1H), 6.91 (dd, J=1.83, 8.54 Hz, 1H), 4.05 (s, 3H), 3.29-3.40 (m, 2H), 3.25 (s, 3H), 3.07-3.20 (m, 2H), 1.89 (ddd, J=5.49, 7.78, 10.83 Hz, 1H), 1.62-1.73 (m, 2H), 1.47-1.57 (m, 1H), 1.31-1.42 (m, 1H), 0.85 (d, J=6.41 Hz, 3H).

Example 16
N-(1-methyl-1H-indazol-6-yl)hexane-3-sulfonamide $^1$H NMR (500 MHz, CDCl3) δ 7.93 (s, 1H), 7.66 (d, J=8.5 Hz, 1H), 7.39 (s, 1H), 6.85 (dd, J=1.83, 8.5 Hz, 1H), 6.57 (br s, 1H), 4.05 (s, 3H), 3.02 (quin, J=5.8 Hz, 1H), 1.74-1.98 (m, 4H), 1.45-1.57 (m, 1H), 1.33-1.45 (m, 1H), 1.03 (t, J=7.5 Hz, 3H), 0.89 (t, J=7.3 Hz, 3H).

Example 17
N-(1-methyl-1H-indazol-6-yl)pentane-2-sulfonamide $^1$H NMR (500 MHz, CDCl3) δ 7.93 (s, 1H), 7.66 (d, J=8.5 Hz, 1H), 7.39 (s, 1H), 6.89 (d, J=8.5 Hz, 1H), 6.78 (s, 1H), 4.05 (s, 3H), 3.12-3.24 (m, 1H), 1.92-2.06 (m, 1H), 1.56-

1.69 (m, 1H), 1.46-1.56 (m, 1H), 1.36-1.42 (m, 3H), 1.25-1.35 (m, 1H), 0.89 (t, J=7.3 Hz, 3H).

Example 18 4-methyl-N-(1-methyl-1H-indazol-6-yl)pentane-1-sulfonamide

¹H NMR (500 MHz, CDCl3) δ 7.94 (s, 1H), 7.67 (d, J=8.54 Hz, 1H), 7.39 (s, 1H), 6.87 (dd, J=1.68, 8.70 Hz, 1H), 6.76 (br s, 1H), 4.06 (s, 3H), 3.01-3.14 (m, 2H), 1.76-1.90 (m, 2H), 1.51 (quind, J=6.64, 13.41 Hz, 1H), 1.22-1.29 (m, 2H), 0.85 (d, J=6.41 Hz, 6H).

Example 19 4-methyl-N-(1-methyl-1H-indazol-6-yl)benzenesulfonamide

¹H NMR (500 MHz, CD3OD) δ 7.87 (br s, 1H), 7.67 (d, J=6.4 Hz, 2H), 7.56 (d, J=8.5 Hz, 1H), 7.23-7.31 (m, 3H), 6.86 (d, J=8.5 Hz, 1H), 3.95 (br s, 3H), 2.34 (br s, 3H).

Example 20 N-(1-methyl-1H-indazol-6-yl)-1-phenylmethanesulfonamide

¹H NMR (500 MHz, CDCl3) δ 7.93 (s, 1H), 7.62-7.73 (m, 1H), 7.27-7.41 (m, 5H), 6.72 (d, J=8.5 Hz, 1H), 6.57 (br s, 1H), 4.38 (s, 2H), 4.03 (s, 3H).

Example 21 N-(1-methyl-1H-indazol-6-yl)-2-phenylethane-1-sulfonamide

¹H NMR (500 MHz, CDCl3) δ 7.93 (s, 1H), 7.62 (d, J=8.5 Hz, 1H), 7.26-7.33 (m, 3H), 7.20 (s, 1H), 7.15 (d, J=7.3 Hz, 2H), 6.65 (d, J=8.5 Hz, 1H), 6.42 (s, 1H), 4.04 (s, 3H), 3.39 (t, J=7.6 Hz, 2H), 3.16 (t, J=7.6 Hz, 2H).

Example 22 N-(1-methyl-1H-indazol-6-yl)cyclopropanesulfonamide

¹H NMR (500 MHz, CDCl3) δ 7.95 (s, 1H), 7.67 (d, J=8.5 Hz, 1H), 7.41 (s, 1H), 6.95 (dd, J=1.9, 8.4 Hz, 1H), 6.60 (s, 1H), 4.06 (s, 3H), 2.46-2.59 (m, 1H), 1.16-1.23 (m, 2H), 0.91-1.01 (m, 2H).

Example 23 N-(1-methyl-1H-indazol-6-yl)cyclobutanesulfonamide

¹H NMR (500 MHz, CDCl3) δ 7.93 (s, 1H), 7.65 (d, J=8.54 Hz, 1H), 7.37 (s, 1H), 6.86 (d, J=8.55 Hz, 1H), 6.75 (br s, 1H), 4.05 (s, 3H), 3.94 (quin, J=8.32 Hz, 1H), 2.52-2.63 (m, 2H), 2.20-2.30 (m, 2H), 1.91-2.05 (m, 2H).

Example 24 N-(1-methyl-1H-indazol-6-yl)cyclopentanesulfonamide

¹H NMR (500 MHz, CDCl3) δ 7.93 (s, 1H), 7.66 (d, J=8.24 Hz, 1H), 7.41 (s, 1H), 6.87 (d, J=8.54 Hz, 1H), 6.54 (s, 1H), 4.05 (s, 3H), 3.50-3.62 (m, 1H), 1.93-2.14 (m, 5H), 1.78-1.87 (m, 2H), 1.58-1.64 (m, 2H).

Example 25 N-(1-methyl-1H-indazol-6-yl)cyclohexanesulfonamide

¹H NMR (500 MHz, CDCl3) δ 7.93 (s, 1H), 7.66 (d, J=8.54 Hz, 1H), 7.40 (s, 1H), 6.86 (d, J=8.54 Hz, 1H), 6.52 (s, 1H), 4.05 (s, 3H), 2.97-3.11 (m, 1H), 2.17 (d, J=12.82 Hz, 2H), 1.82-1.91 (m, 2H), 1.58-1.70 (m, 3H), 1.14-1.23 (m, 3H).

Example 26 N-(1-methyl-1H-indazol-6-yl)-4-(trifluoromethyl)cyclohexane-1-sulfonamide ¹H NMR (500 MHz, CDCl3) δ 7.94 (s, 1H), 7.67 (d, J=8.54 Hz, 1H), 7.39 (s, 1H), 6.87 (dd, J=1.83, 8.54 Hz, 1H), 6.65 (s, 1H), 4.05 (s, 3H), 3.22 (quin, J=5.57 Hz, 1H), 2.20-2.27 (m, 2H), 2.05-2.18 (m, 3H), 1.82-1.93 (m, 2H), 1.67-1.75 (m, 2H).

Example 27 N-(1-methyl-1H-indazol-6-yl)piperidine-1-sulfonamide

¹H NMR (500 MHz, CDCl3) δ 7.92 (s, 1H), 7.63 (d, J=8.54 Hz, 1H), 7.30 (s, 1H), 7.01 (br s, 1H), 6.90 (dd, J=1.53, 8.54 Hz, 1H), 4.04 (s, 3H), 3.21-3.31 (m, 4H), 1.50-1.57 (m, 4H), 1.43-1.50 (m, 2H).

Example 28 1-cyclohexyl-N-(1-methyl-1H-indazol-6-yl)methanesulfonamide

¹H NMR (500 MHz, CDCl3) δ 7.94 (s, 1H), 7.67 (d, J=8.24 Hz, 1H), 7.37 (s, 1H), 6.87 (d, J=8.54 Hz, 1H), 6.81 (s, 1H), 4.05 (s, 3H), 3.01 (d, J=6.10 Hz, 2H), 1.99-2.13 (m, 1H), 1.87-1.99 (m, J=12.50 Hz, 2H), 1.64-1.75 (m, J=13.40 Hz, 2H), 1.21-1.36 (m, 2H), 0.98-1.21 (m, 3H).

Example 29 N-(1-(methyl-d3)-1H-indazol-6-yl)butane-1-sulfonamide

¹H NMR (500 MHz, CDCl3) δ 7.95 (s, 1H), 7.68 (d, J=8.5 Hz, 1H), 7.37-7.44 (m, 1H), 6.89 (dd, J=2.14, 8.5 Hz, 1H), 6.80 (br s, 1H), 3.10-3.17 (m, 2H), 1.78-1.87 (m, 2H), 1.41 (qd, J=7.5, 14.9 Hz, 2H), 0.90 (t, J=7.3 Hz, 3H).

Example 30 N-(1-(methyl-d3)-1H-indazol-6-yl)pentane-1-sulfonamide

¹H NMR (500 MHz, CDCl3) δ 7.95 (s, 1H), 7.67 (d, J=8.5 Hz, 1H), 7.38 (s, 1H), 6.87 (d, J=8.5 Hz, 1H), 6.70 (s, 1H), 3.06-3.17 (m, 2H), 1.84 (quint, J=7.5 Hz, 2H), 1.22-1.42 (m, 4H), 0.86 (t, J=7.0 Hz, 3H).

Example 31 4-methoxy-N-(1-(methyl-d3)-1H-indazol-6-yl)butane-1-sulfonamide

¹H NMR (500 MHz, CDCl3) δ 7.94 (s, 1H), 7.67 (d, J=8.54 Hz, 1H), 7.38 (s, 1H), 6.87 (d, J=8.54 Hz, 1H), 6.70 (br s, 1H), 3.35 (t, J=5.80 Hz, 2H), 3.26 (s, 3H), 3.17 (t, J=7.48 Hz, 2H), 1.87-2.02 (m, 2H), 1.53-1.72 (m, 2H+1H from H2O).

Example 32 Synthesis of N-methyl-N-(1-methyl-1H-indazol-6-yl)butane-1-sulfonamide To a vigorously stirring, ice cold solution of N-(1-methyl-1H-indazol-6-yl)butane-1-sulfonamide (78.8 mg, 0.295 mmol) in dimethylformamide (3 mL), NaH (47.2 mg, 1.18 mmol) was added in four portions. The reaction mixture was maintained at 0° C. for 30 min and then warmed to room temperature. Iodomethane (73.5 μL, 1.18 mmol) was added dropwise to the reaction mixture and the reaction was stirred for 16 hours. The reaction mixture was quenched with water and diluted with ethyl acetate. The reaction mixture was transferred to a separatory funnel, washed with water three times and dried over anhydrous magnesium sulfate. The reaction mixture was concentrated on a rotary evaporator and the residue was purified by flash chromatography on silica using ethyl acetate as eluent to afford the product as a yellow solid (70 mg, 85% yield): $^1$H NMR (500 MHz, CDCl3) δ 7.97 (s, 1H), 7.72 (d, J=8.5 Hz, 1H), 7.48 (s, 1H), 7.13 (d, J=8.5 Hz, 1H), 4.07 (s, 3H), 3.42 (s, 3H), 2.96-3.06 (m, 2H), 1.82 (m, 2H), 1.42 (m, 2H), 0.92 (t, J=7.32 Hz, 3H).

Example 33 Synthesis of 1-Butyl-3-(1-methyl-1H-indazol-6-yl)thiourea

To a solution of 1-methyl-1H-indazol-6-amine (27 mg, 0.183 mmol) in pyridine (1 mL), was added n-butylisothiocyanate (25 μL, 0.2 mmol) and the reaction was stirred at room temperature for 14 h. After completion of the reaction, the reaction mixture was diluted with ethyl acetate, transferred to a separatory funnel and washed with water, saturated sodium bicarbonate solution, and brine. The organic layer was dried over anhydrous magnesium sulfate and concentrated via rotary evaporator. The crude product was purified by flash chromatography on silica gel (gradient: 0-70% ethyl acetate/hexanes) to obtain the product as a white solid (34.6 mg, 72% yield): $^1$H NMR (500 MHz, CDCl3) δ 8.00 (s, 1H), 7.77 (d, J=8.2 Hz, 2H), 6.98 (dd, J=1.2, 8.5 Hz, 1H), 6.05 (br s, 1H), 4.06 (s, 3H), 3.60-3.69 (m, 2H), 1.50-1.60 (m, 2H), 1.33 (qd, J=7.4, 15.0 Hz, 2H), 0.92 (t, J=7.3 Hz, 3H).

Example 34 Synthesis of 1-Butyl-3-(1-methyl-1H-indazol-6-yl)urea

To a solution of 1-methyl-1H-indazol-6-amine (30 mg, 0.204 mmol) in pyridine (1 mL), was added n-butylisocyanate (25.2 μL, 0.224 mmol) and the reaction was stirred at room temperature for 14 hours. After completion of the reaction, the reaction mixture was diluted with ethyl acetate, transferred to a separatory funnel and washed with water, saturated sodium bicarbonate solution, and brine. The organic layer was dried over anhydrous magnesium sulfate and concentrated in vacuo. The crude product was purified by flash chromatography on silica gel (gradient: 0-70% ethyl acetate/hexanes) to obtain the product as a white solid (49.7 mg, 98% yield): $^1$H NMR (500 MHz, CDCl3) δ 7.88 (s, 1H), 7.78 (s, 1H), 7.56 (dd, J=4.9, 7.9 Hz, 1H), 6.64-6.92 (m, 2H), 4.71-5.10 (m, 1H), 3.99 (d, J=4.3 Hz, 3H), 3.22-3.33 (m, 2H), 1.44-1.56 (m, 2H), 1.29-1.41 (m, 2H), 0.83-0.99 (m, 3H).

Example 35 Synthesis of N-(1-methyl-1H-indazol-6-yl)propionamide

Using a procedure similar to that described in Example 36, the title compound was prepared: $^1$H NMR (500 MHz, CDCl3) δ 8.19 (br s, 1H), 7.88 (s, 1H), 7.78 (m, 1H), 7.57 (d, J=8.54 Hz, 1H), 6.83 (d, J=8.54 Hz, 1H), 3.99 (s, 3H), 2.44 (q, J=7.32 Hz, 2H), 1.26 (t, J=7.48 Hz, 3H).

Example 36 Synthesis of N-(1-methyl-1H-indazol-6-yl)pentanamide

To a solution of 1-methyl-1H-indazol-6-amine (19 mg, 0.13 mmol) in dichloromethane (1 mL) was added triethylamine (20 μL, 0.142 mmol). To this mixture, pentanoyl chloride (17 μL, 0.142 mmol) was added dropwise at 0° C. The reaction was allowed to warm to room temperature and was then stirred for 16 hours. After completion of the reaction, the reaction mixture was diluted with ethyl acetate and transferred to a separatory funnel. The organic layer was washed with saturated aqueous sodium bicarbonate solution, followed by water, and brine. The organic layer was dried over anhydrous magnesium sulfate, filtered and concentrated in vacuo. The crude product was purified by flash chromatography on silica gel (gradient: 0-70% ethyl acetate/hexanes) to obtain the product as a white solid (22.5 mg, 75% yield): $^1$H NMR (500 MHz, d6-acetone) δ 9.26 (br s, 1H), 8.24 (s, 1H), 7.84 (s, 1H), 7.61 (d, J=8.5 Hz, 1H), 7.08 (dd, J=1.7, 8.7 Hz, 1H), 4.00 (s, 3H), 2.41 (t, J=7.48 Hz, 2H), 1.68 (quin, J=7.55 Hz, 2H), 1.40 (qd, J=7.4, 14.9 Hz, 2H), 0.93 (t, J=7.5 Hz, 3H).

Example 37 Synthesis of Ethyl (1-methyl-1H-indazol-6-yl)carbamate

To a solution of 1-methyl-1H-indazol-6-amine (35.6 mg, 0.241 mmol) in dichloromethane (2 mL) was added triethylamine (36.8 μL, 0.264 mmol). Ethyl chloroformate (25.3 μL, 0.264 mmol) was then added dropwise at 0° C. and the reaction was allowed to warm to room temperature. After 16 hours, the reaction mixture was diluted with ethyl acetate and transferred to a separatory funnel. The organic layer was washed with saturated aqueous sodium bicarbonate solution, followed by water, and brine. The organic layer was dried over anhydrous magnesium sulfate, filtered and concentrated in vacuo. The crude product was purified by flash chromatography on silica gel (gradient: 0-70% ethyl acetate/hexanes) to obtain the product as a white solid (28.3 mg, 54% yield): $^1$H NMR (500 MHz, CDCl3) δ 7.89 (s, 2), 7.59 (d, J=8.5 Hz, 1H), 6.73-6.83 (m, 2H), 4.27 (q, J=7.0 Hz, 2H), 4.03 (s, 3H), 1.34 (t, J=7.2 Hz, 3H).

Example 38 Synthesis of n-propyl (1-methyl-1H-indazol-6-yl)carbamate

Using a procedure similar to that described in Example 39, the title compound was prepared (24.2 mg, 76% yield): $^1$H NMR (500 MHz, CDCl3) δ 7.89 (s, 1H), 7.59 (d, J=8.54 Hz, 1H), 6.78 (dd, J=1.53, 8.54 Hz, 2H), 4.17 (t, J=6.71 Hz, 2H), 4.03 (s, 3H), 1.73 (sxt, J=7.14 Hz, 2H), 1.00 (t, J=7.32 Hz, 3H).

Example 39 Synthesis of Butyl (1-methyl-1H-indazol-6-yl)carbamate

A solution of 1-methyl-1H-indazol-6-amine (12.5 mg, 0.084 mmol) and 1,1'-carbonyldiimidazole (15.0 mg, 0.093 mmol) in dichloromethane (1 mL) was stirred under reflux conditions for 4 hours. After the starting material was consumed, n-butanol (1 mL) was added and the reaction was refluxed for an additional 12 h. After completion of the reaction, the reaction mixture was concentrated in vacuo. The crude product was purified by flash chromatography on silica gel (gradient: 0-70% ethyl acetate/hexanes) to afford the product as a white solid (16.5 mg, 79% yield): $^1$H NMR (500 MHz, CDCl3) δ 7.82 (s, 1H), 7.53 (d, J=8.54 Hz, 1H), 6.65-6.74 (m, 2H), 4.14 (t, J=6.56 Hz, 2H), 3.96 (s, 3H), 1.50-1.68 (m, 2H+H from H2O), 1.38 (qd, J=7.40, 15.03 Hz, 2H), 0.90 (t, J=7.32 Hz, 3H).

Example 40 Synthesis of 1-Methyl-N-pentyl-1H-indazol-6-amine

To a solution of 36 (FIG. 7, 14.4 mg, 0.06 mmol) in tetrahydrofuran (0.5 mL) was added lithium aluminum hydride (0.12 mL of 1 M solution in tetrahydrofuran, 0.12 mmol) dropwise at 0° C. The reaction was allowed to warm to room temperature and was then stirred for 16 hours. After completion of the reaction, the reaction mixture was diluted with ethyl acetate and transferred to a separatory funnel. The organic layer was washed with saturated aqueous sodium bicarbonate solution, followed by water, and brine. The organic layer was dried over anhydrous magnesium sulfate, filtered and concentrated. The crude product was purified by flash chromatography on silica gel (gradient: 0-70% ethyl acetate/hexanes) to obtain the product as a white solid (12.4 mg, 95% yield): $^1$H NMR (500 MHz, CDCl3) δ 7.76 (s, 1H), 7.43 (d, J=8.54 Hz, 1H), 6.48 (dd, J=1.83, 8.85 Hz, 1H), 6.30 (s, 1H), 3.95 (s, 3H), 3.17 (t, J=7.17 Hz, 2H), 1.69 (quin, J=7.17 Hz, 2H), 1.31-1.49 (m, 4H), 0.94 (t, J=7.02 Hz, 3H).

Example 41 Synthesis of N-(3-methyl-1H-indazol-5-yl)butane-1-sulfonamide

To a solution of 4h (FIG. 7, 30 mg, 0.20 mmol) in pyridine (1 mL) was added n-butyl sulfonyl chloride (29 μL, 0.22 mmol) and the reaction was stirred at room temperature for 16 hours. After completion of the reaction, the reaction mixture was diluted with ethyl acetate and transferred to a separatory funnel. The organic layer was washed with saturated aqueous sodium bicarbonate solution, followed by water, and brine. The organic layer was dried over anhydrous magnesium sulfate, filtered and concentrated. The crude product was purified by flash chromatography on silica gel (gradient: 30-70% ethyl acetate/hexanes) to obtain the product as a white solid (36.8 mg, 69% yield): $^1$H NMR (500 MHz, CDCl$_3$) δ 7.60 (s, 1), 7.44 (d, J=8.85 Hz, 1), 7.28 (s, 1), 6.43 (br s, 1), 2.95-3.14 (m, 2), 2.60 (s, 3), 1.77-1.90 (m, 1), 1.35-1.53 (m, 2), 0.91 (t, J=7.32 Hz, 3).

Examples 42-53

Using procedures similar to those described herein, the following representative compounds of the invention were also prepared.

42
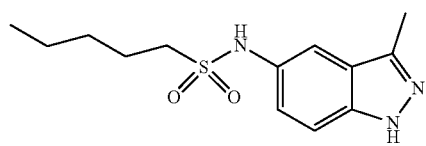

43
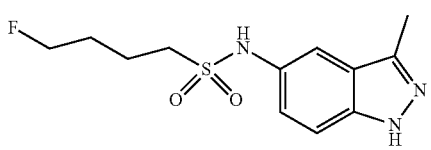

44
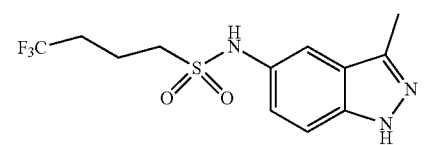

45
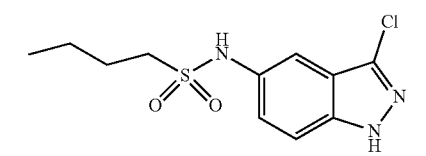

46
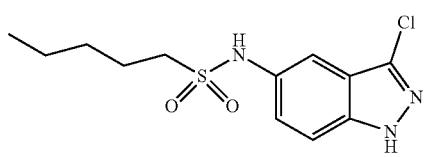

47
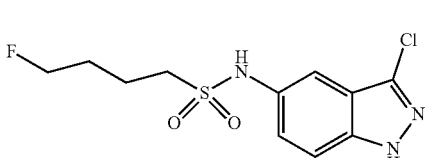

48
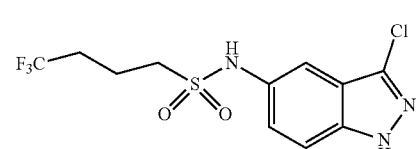

49
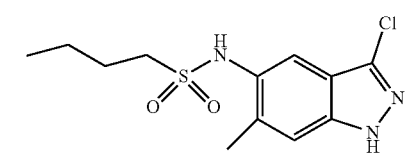

50
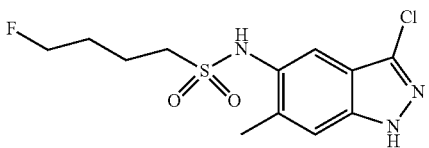

51
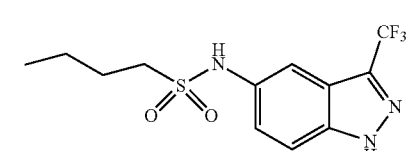

52
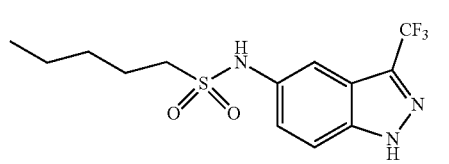

and

53
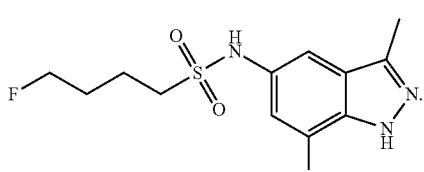

Example 42 Synthesis of N-(3-methyl-1H-indazol-5-yl)pentane-1-sulfonamide

Using a procedure similar to that described in Example 41, the title compound was prepared: $^1$H NMR (500 MHz, CDCl$_3$) δ 7.59 (s, 1H), 7.42 (d, J=8.5 Hz, 1H), 7.28 (br s, 1H+CDCl$_3$), 6.70 (s, 1H), 2.99-3.11 (m, 2H), 2.59 (s, 3H), 1.80-1.93 (m, 2H), 1.19-1.42 (m, 4H), 0.87 (t, J=5.9 Hz, 3H).

Example 43 Synthesis of 4-Fluoro-N-(3-methyl-1H-indazol-5-yl)butane-1-sulfonamide The following scheme illustrates the synthesis of Examples 43 and 45.

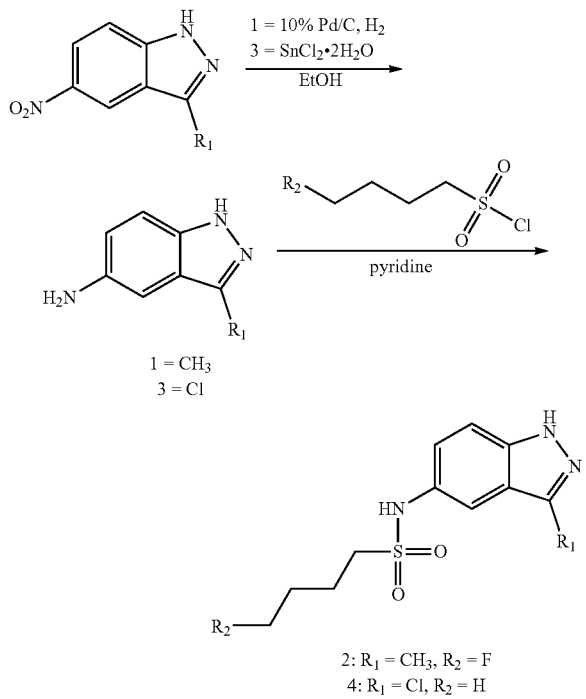

a. Preparation of:

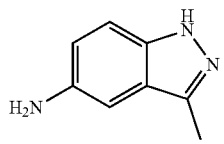

5-Nitro-3-methyl-1H-indazole (1.03 g, 5.81 mmol; Synthonix) was placed into an oven-dried round bottom flask, followed by the 10% Pd/C (0.1 wt %; Sigma Aldrich). The reagents were suspended in 30 mL of anhydrous ethanol (Fisher Scientific) and equipped with a balloon with $H_2$. The reaction proceeded for 64 h at room temperature, after which the reaction was filtered and concentrated to yield 5-amino-3-methyl-1H-indazole as a tan solid (658 mg, 77% yield). The reaction product was judged satisfactory by LC-MS and used without $^1$H NMR characterization.

b. Preparation of:

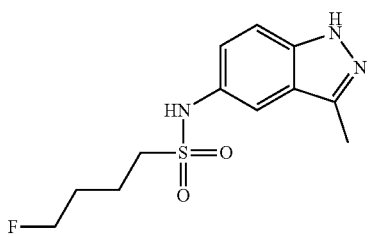 [SMILES: Cc1n[nH]c2ccc(NS(=O)(=O)CCCCF)cc12]

5-Amino-3-methyl-1H-indazole (658 mg, 4.48 mmol) was placed into an oven-dried round bottom flask, and suspended in 30 mL of anhydrous pyridine (Sigma Aldrich). The mixture was cooled down to 0° C. and then 4-fluorobutanesulfonyl chloride (742 mg, 4.25 mmol; Enamine) was added dropwise by syringe. The reaction was allowed to proceed overnight, after which it was concentrated into a dark burgundy residue. The residue was suspended in ethyl acetate and 0.1 N $HCl_{(aq)}$, extracted three times with ethyl acetate and washed with brine. The organic fraction was harvested, dried over $Na_2SO_4$ (Fisher Scientific), and finally concentrated. The product was purified by flash column chromatography (40 g column, 0%→100% ethyl acetate: hexanes). The title compound was obtained as an off-white solid (1.02 g, 85% yield). $[M+H]^+$=286.0. H NMR (500 MHz, $d_6$-DMSO) δ 12.64 (s, 1), 9.58 (s, 1), 7.48 (d, J=1.4 Hz, 1), 7.43 (d, J=8.8 Hz, 1), 7.22 (dd, J=8.8, 1.7 Hz, 1), 4.47 (t, J=5.5 Hz, 1), 4.37 (t, J=5.8 Hz, 1), 3.10-3.01 (m, 2), 2.45 (s, 3), 1.83-1.66 (m, 4).

Example 44 Synthesis of 4,4,4-trifluoro-N-(3-methyl-1H-indazol-5-yl)butane-1-sulfonamide Using a procedure similar to that described in Example 41, the title compound was prepared: $^1$H NMR (500 MHz, MeOD) δ 7.58 (d, J=1.2 Hz, 1H), 7.45 (d, J=8.8 Hz, 1H), 7.31 (dd, J=8.8, 1.8 Hz, 1H), 3.14 (t, J=7.6 Hz, 2H), 2.53 (s, 3H), 2.23-2.43 (m, 2H), 1.95-2.11 (m, 2H).

Synthesis of 3-chloro-1H-indazol-5-amine (10)

To a solution of 2-methyl-4-nitroaniline (298 mg, 1.96 mmol), in acetic acid maintained at 0° C. was added dropwise sodium nitrite (135.2 mg, 1.96 mmol) dissolved in water. The reaction was stirred at room temperature for 72 h. The reaction mixture was concentrated on rotary evaporator and the residue was diluted with ethyl acetate and washed with saturated aqueous sodium bicarbonate solution and brine. The organic layer was dried over anhydrous magnesium sulfate, filtered, and concentrated in vacuo to yield 5-nitro-1H-indazole (6) in quantitative yield.

To a solution of sodium hydroxide (274 g, 6.84 mmol) in $H_2O$ (8 mL) was added 5-nitroindazole (6) (280 mg, 1.71 mmol), and the mixture was heated until a red solution formed. The mixture was cooled in an ice-water bath for 15 minutes, sodium hypochlorite (3.3 mL, 5.25%, 2.5 mmol) was added and the mixture stirred at 0° C. for 12 h after which the pH was adjusted to 7 with diluted HC. The mixture was extracted with ethyl acetate, and the combined organic layer washed with water and concentrated under reduced pressure. The residue was purified by flash chromatography to provide 3-chloro-5-nitro-1H-indazole (7) (310 mg, 92% yield). m/z 198 $[M+H]^+$.

To a solution of 3-chloro-5-nitro-1H-indazole (7) (310 mg, 1.57 mmol) in ethanol (150 mL) was added stannous chloride dihydrate (1.77 g, 7.85 mmol). The reaction mixture was refluxed for 4 h. After completion of reaction, the mixture was concentrated on rotary evaporator. The residue was diluted with dichloromethane and basified with sodium hydroxide. The mixture was transferred to separatory funnel and the aqueous layer was extracted with dichloromethane The combined organic layer was dried over anhydrous magnesium sulfate, filtered, and concentrated in vacuo. The residue was purified by flash chromatography to provide 3-chloro-1H-indazol-5-amine (10) (186 mg, 71 yield). m/z 168 $[M+H]^+$.

Example 45 Synthesis of N-(3-chloro-1H-indazol-5-yl)butane-1-sulfonamide a. Preparation of:

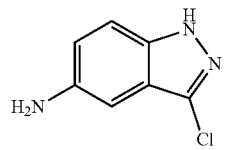 [SMILES: Nc1ccc2[nH]nc(Cl)c2c1]

3-Chloro-5-nitro-1H-indazole (800 mg, 4.06 mmol; Combi-Blocks) was placed into an oven-dried round bottom flask, followed by the addition of stannous chloride dehydrate (4.50 g, 20.0 mmol; Acros Organics). The reaction mixture was suspended in 40 mL of anhydrous ethanol and proceeded overnight at room temperature. The mixture was then concentrated, extracted three times with ethyl acetate and washed once with brine. The organic layer was dried over $Na_2SO_4$, filtered and then concentrated to yield 5-amino-3-chloro-1H-indazole as an off-white solid (644 mg, 95% yield). The reaction product was judged satisfactory by LC-MS and used without $^1$H NMR characterization.

b. Preparation of:

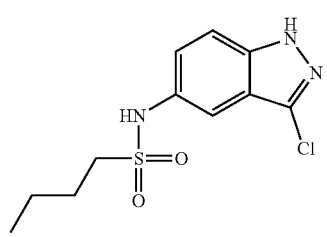 [SMILES: CCCCS(=O)(=O)Nc1ccc2[nH]nc(Cl)c2c1]

5-Amino-3-chloro-1H-indazole (644 mg, 3.86 mmol) was placed into an oven-dried round bottom flask, and suspended in 10 mL of anhydrous pyridine. The mixture was cooled down to 0° C. and then 1-butanesulfonyl chloride (498 µL, 3.86 mmol; Enamine) was added dropwise by syringe. The reaction proceeded overnight after which it was concentrated, extracted three times with ethyl acetate, washed once with brine, and dried over $Na_2SO_4$. The organic layer was concentrated and purified by flash column chromatography (40 g column, 0% to 100% ethyl acetate:hexanes). The title compound was obtained as a white solid (307 mg, 28% yield). $[M+H]^+$=288.0. $^1$H NMR (500 MHz, CDCl$_3$) δ 10.0 (br s, 1H), 7.56 (br s, 1H), 7.45 (d, J=8.5 Hz, 1H), 7.38 (d, J=8.5 Hz, 1H), 6.55 (br s, 1H), 3.02-3.15 (m, 2H), 1.77-1.89 (m, 2H), 1.36-1.49 (m, 2H), 0.92 (t, J=6.7 Hz, 3H).

Example 46 Synthesis of N-(3-chloro-1H-indazol-5-yl)pentane-1-sulfonamide

Using a procedure similar to that described in Example 45, the title compound was prepared: $^1$H NMR (500 MHz, CDCl$_3$) δ 10.1 (br s, 1H), 7.57 (s, 1H), 7.46 (d, J=8.8 Hz, 1H), 7.39 (d, J=8.8 Hz, 1H), 6.62 (s, 1H), 2.94-3.16 (m, 2H), 1.86 (quin, J=7.6 Hz, 2H), 1.28-1.42 (m, 4H), 0.88 (t, J=7.2 Hz, 3H).

Example 47 Synthesis of N-(3-chloro-1H-indazol-5-yl)-4-fluorobutane-1-sulfonamide Using a procedure similar to that described in Example 45, the title compound was prepared: $^1$H NMR (500 MHz, CDCl$_3$) δ 9.94 (br s, 1H), 7.58 (s, 1H), 7.47 (d, J=8.8 Hz, 1H), 7.39 (dd, J=2.1, 8.8 Hz, 1H), 6.47 (s, 1H), 4.47-4.56 (m, 1H), 4.37-4.45 (m, 1H), 3.11-3.21 (m, 2H), 2.03 (td, J=7.5, 15.4 Hz, 2H), 1.76-1.92 (m, 2H)

Example 48 Synthesis of N-(3-chloro-1H-indazol-5-yl)-4,4,4-trifluorobutane-1-sulfonamide Using a procedure similar to that described in Example 45, the title compound was prepared: $^1$H NMR (500 MHz, CDCl$_3$) δ 9.92 (br s, 1H), 7.58 (s, 1H), 7.48 (d, J=9.2 Hz, 1H), 7.35-7.40 (m, 1H), 6.43 (br s, 1H), 3.17 (t, J=7.5 Hz, 2H), 2.23-2.45 (m, 2H), 2.15 (quin, J=7.5 Hz, 2H).

Example 49 Synthesis of N-(3-chloro-6-methyl-1H-indazol-5-yl)butane-1-sulfonamide Using a procedure similar to that described in Example 45, the title compound was prepared: $^1$H NMR (500 MHz, CDCl$_3$) δ 9.79 (br s, 1H), 7.70 (s, 1H), 7.33 (s, 1H), 6.06 (s, 1H), 3.06-3.24 (m, 2H), 2.49 (s, 3H), 1.79-1.98 (m, 2H), 1.41-1.52 (m, 2H), 0.95 (t, J=7.3 Hz, 3H).

Example 50 Synthesis of N-(3-chloro-6-methyl-1H-indazol-5-yl)-4-fluorobutane-1-sulfonamide Using a procedure similar to that described in Example 45, the title compound was prepared: $^1$H NMR (500 MHz, CDCl$_3$) δ 9.82 (br s, 1H), 7.70 (s, 1H), 7.33 (s, 1H), 6.12 (s, 1H), 4.53 (t, J=5.6 Hz, 1H), 4.44 (t, J=5.6 Hz, 1H), 3.16-3.32 (m, 2H), 2.06 (td, J=15.3, 7.6, Hz, 2H), 1.75-1.97 (m, 2H).

Example 51 Synthesis of N-(3-trifluoromethyl-1H-indazol-5-yl)butane-1-sulfonamide Using a procedure similar to that described in Example 45, the title compound was prepared: $^1$H NMR (500 MHz, CDCl$_3$) δ 10.4 (br s, 1), 7.66 (s, 1), 7.58 (d, J=9.2 Hz, 1), 7.49 (dd, J=9.0, 1.7, Hz, 1), 6.41 (s, 1), 3.01-3.19 (m, 2), 1.77-1.92 (m, 2), 1.44 (qd, J=14.9, 7.4 Hz, 2), 0.92 (t, J=7.5 Hz, 3).

Example 52 Synthesis of N-(3-trifluoromethyl-1H-indazol-5-yl)pentane-1-sulfonamide Using a procedure similar to that described in Example 45, the title compound was prepared: $^1$H NMR (500 MHz, CDCl$_3$) δ 10.7 (br s, 1), 7.67 (s, 1), 7.58 (d, J=9.2 Hz, 1), 7.49 (dd, J=8.8, 1.8 Hz, 1), 6.75 (br s, 1), 3.05-3.16 (m, 2), 1.86 (td, J=15.5, 7.8 Hz, 2), 1.26-1.43 (m, 4), 0.87 (t, J=7.2 Hz, 3).

Example 53 Synthesis of N-(7-fluoro-3-methyl-1H-indazol-5-yl)-4-fluorobutane-1-sulfonamide Using a procedure similar to that described in Example 45, the title compound was prepared: $^1$H NMR (500 MHz, d$_6$-DMSO) δ 13.2 (br s, 1), 9.75 (s, 1), 7.31 (s, 1), 7.06 (d, J=12.5 Hz, 1), 4.46 (t, J=10.5 Hz, 1), 4.37 (t, J=11.5 Hz, 1), 3.11 (t, J=15 Hz, 2), 2.46 (s, 3), 1.78 (q, J=17.5 Hz, 3), 1.69 (t, J=13.5 Hz, 1).

Example 54 Biological Data

DG167 is an Inhibitor of *M. tuberculosis* KasA.

A library of 168 compounds with established antitubercular whole-cell efficacy for putative cell-wall inhibitors was screened using a previously described *M. bovis* BCG strain harboring a lacZ reporter fused to the *M. tuberculosis* iniBAC promoter (PiniBAC)(Alland et al., 2000; Tahlan et al., 2012; Wilson et al., 2013). $GSK3011724_A$ (Ballell, L., et al., *Chem Med Chem,* 2013, 8, 313-321) (renamed DG167) was found to be one of the top inducers of iniBAC promoter (approximately 12 fold), suggesting that DG167 was likely to inhibit a component of cell-wall biosynthesis. DG167 possessed potent whole-cell activity against *M. tuberculosis* with a minimum inhibitory concentration ($MIC_{90}$) of 0.39 μM. Activity was preserved against both drug-susceptible and drug-resistant clinical *M. tuberculosis* strains and against *M. tuberculosis* strains resistant to MmpL3 inhibitors such as SQ109 suggesting a novel target for DG167 (Table 1, FIG. 1). Interestingly, DG167 lacked whole-cell activity (MIC>100 μM) against nontuberculous mycobacteria (NTMs) such as *M. abscessus, M. fortuitum, M. avium, M. smegmatis* and *M. marinum* (Table 1). DG167-resistant *M. tuberculosis* mutants were selected to gain insights into its molecular target. All seven DG167-resistant mutants analyzed (MIC shift of 4 to >256×) remained susceptible to INH, EMB, ETH, rifampicin (Rif), moxifloxacin (Moxi), PA824, SQ109, and BDQ (Table 2, FIG. 2). Whole-genome sequencing (WGS) of each mutant identified a unique single-nucleotide polymorphism (SNP) in the *M. tuberculosis* kasA gene (Table 2). Computational docking studies with the known KasA structure (Luckner, S. R., et al., *Structure,* 2009, 17, 1004-1013) were performed, and DG167 was predicted to bind the KasA substrate-binding site.

KasA-DG167 Crystal Structure Reveals Unique Dual Binding to Interacting Nonidentical Sites in the KasA Substrate-Binding Channel.

The X-ray crystal structure of KasA in complex with DG167 was solved to gain insights into the DG167 mechanism of action. *M. tuberculosis* KasA was overexpressed and purified from the mycobacterial host *M. smegmatis* and the KasA-DG167 co-crystal structure was refined to 2.00 Å resolution. The crystal structure of apo KasA, which was refined to 1.80 Å resolution using crystallization conditions similar to those used to crystallize KasA-DG167 was also determined. Each KasA monomer was found to bind to two DG167 molecules ($KasA\text{-}DG167_2$), with the result that the biological KasA dimer bound four DG167 molecules, i.e., KasA binds $DG167_A$ and $DG167_B$, and KasA' binds $DG167_{A'}$ and $DG167_{B}$. The clearly interpretable electron density corresponding to $DG167_A$ and $DG167_B$ showed the two DG167 molecules bound to non-overlapping sites in the KasA acyl channel identified as the phospholipid (PL) binding site observed in previous crystal structures (Luckner, S. R., et al., *Structure,* 2009, 17, 1004-1013). Consistent with the $KasA\text{-}DG167_2$ structure, the KasA mutations identified in the laboratory-generated DG167-resistant *M. tuberculosis* strains mapped near the binding sites of both $DG167_A$ and $DG167_B$. Interestingly, the aliphatic moiety of $DG167_A$ mimics binding of the PL acyl tail as it inserts into a pocket formed by residues Gly200, Ile202, Pro206, Phe239, His345, and Ile347. The $DG167_B$ aliphatic moiety similarly follows the path traced by PL and presumably bona fide acyl substrates (Luckner, S. R., et al., *Structure,* 2009, 17, 1004-1013). The $DG167_A$ and $DG167_B$ indazole groups make hydrophobic interactions throughout the acyl channel and the $DG167_B$ indazole group mediates additional hydrophobic contacts across the KasA/KasA' dimer interface. The $KasA\text{-}DG167_2$ interaction is further stabilized by hydrogen bonds between the $DG167_A$ sulfonamide N—H and Glu199 (FIG. 6A) as well as by the $DG167_B$ indazole group nitrogen and a water molecule coordinated by residues Gly115, Asn148, and Ala170 (FIGS. 6A and 6B). Importantly, the two molecules of DG167 bound to the KasA monomer form an intermolecular hydrogen bond. Specifically, a $DG167_A$ sulfonamide oxygen hydrogen bonds with the $DG167_B$ sulfonamide N—H (FIG. 6B). In sum, an extensive array of both hydrophobic interactions and hydrogen bonds stabilize the binding of two DG167 molecules to a KasA monomer. Moreover, the two DG167 molecules hydrogen bond to each other and occupy the KasA surface that would otherwise bind the elongating acyl chain prior to the condensation reaction catalyzed by KasA. Thus, the $KasA\text{-}DG167_2$ co-crystal structure provides a plausible mechanism by which DG167 can effectively compete for substrate binding, inhibit KasA activity, and produce a bactericidal effect on *M. tuberculosis.*

Biochemical Solution Studies and X-Ray Crystallographic Analysis Show that Dual Inhibitor Binding is not Required to Disrupt KasA Function.

While two molecules of DG167 occupy the acyl channel, it was hypothesized that a single compound bound to the channel would be sufficient to block chain elongation. The X-ray crystal structure of KasA in complex with Example 41 was determined, revealing that Example 41 bound the acyl channel only once and in place of $DG167_A$. It is likely that Example 41 cannot bind in place of DG167B because in a similar pose the Example 41 indazole N(1)-H would be forced to interact with a hydrophobic surface across the KasA dimer interface.

To measure the binding affinity of the DG167 and its analogs to KasA, a microscale thermophoresis (MST) assay was developed. It was determined that the KasA-DG167 interaction has an $EC_{50}$=130.9±18.2 nM. In comparison, Example 41 binds KasA tightly with a Kd=46.5±18.7 nM, while an inactive des-methyl analog, Example 1, bound KasA very weakly with an $EC_{50}$=1736.1±221.2 nM). Consistent with the idea that a single compound bound to the acyl channel is sufficient to block chain elongation, Example 41 displayed 2× improvement over DG167 in MIC against *M. tuberculosis* (MIC=0.20 μM, Table 3, FIG. 3).

DG167 Inhibits Mycolic Acid Biosynthesis.

KasA is an essential component of the FASII complex along with InhA. The effect of DG167 on mycolic acid biosynthesis was studied using a radiolabeled precursor, $^{14}C$-acetate. DG167 exhibited dose-dependent inhibition of mycolic acid biosynthesis (FIGS. 4A and 4C) like INH and inactive des-methyl analog Example 1 (Table 3) did not show any inhibition. Furthermore, a DG167-resistant isolate harboring $KasA_{P206T}$ (DRM167-32×2, Table 2) was found to be resistant to DG167-mediated inhibition of mycolic acid biosynthesis (FIGS. 4B and 4D). Additionally, inhibitors of FAS-II likes INH are known to cause accumulation of FAS-I products and DG167 treatment caused accumulation of $C_{16}$-$C_{26}$ short-chain fatty-acids confirming specific inhibition of FAS-II by DG167.

Synergistic Lethality of DG167 and INH.

INH treatment is known to induce high-level kasA expression in *M. tuberculosis* (Mdluli, K., et al., *Science,* 1998,e 280, 1607-1610; and Vilcheze, C., et al., *Nat Med,* 2006, 12, 1027-1029) which could potentially antagonize the activity of DG167. However, a checkerboard assay revealed that DG167 and INH were additive (ΣFIC=1). Next, the bactericidal activity of DG167 and INH combination was evaluated. *M. tuberculosis* cultures (~107 cells/mL) were treated with either 10× or 20× the MIC of DG167, 10× the MIC of INH, or a combination of both drugs at 10× the MIC of each compound (FIG. 5A). DG167 alone reduced viable colony-forming units (CFU) by 2 log 10 over seven days, and this bactericidal effect was independent of the DG167 concentration tested. Treatment of the cultures with INH alone (10×MIC) resulted in rapid reduction of viable CFU followed by rapid re-growth. This typical pattern of killing and regrowth has been previously attributed to the emergence of persisters combined with the emergence of INH resistant clones (Vilcheze, C., and Jacobs, W. R., Jr., *Antimicrob Agents Chemother*, 2012, 56, 5142-5148; and Wilson, R., et al., *Nat Chem Biol*, 2013, 9, 499-506). Interestingly, the combined use of DG167 and INH markedly improved upon the bactericidal activity of either drug used alone as it produced a rapid reduction in CFU, leading to complete sterilization of these cultures. The synergistic lethality (Malik et al., 2014) observed upon treatment with the DG167-INH combination suggests that simultaneous inhibition of two essential FAS-II targets is strongly bactericidal to *M. tuberculosis*, and that dual FAS-II inhibition may overcome bacterial persistence.

Transcriptional Profiling of *M. tuberculosis* Treated with DG167 and INH Reveals a Unique Signature that Correlates with In Vitro Synergistic Lethality.

Figure 5A:
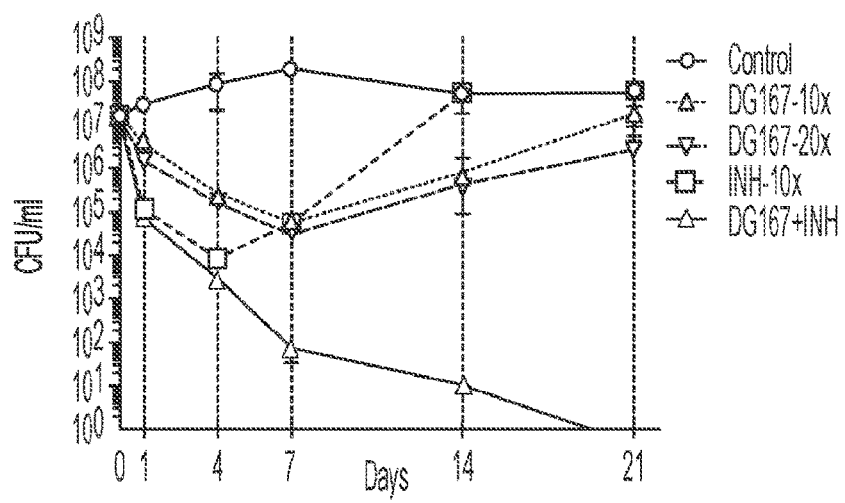
Figure 5B:
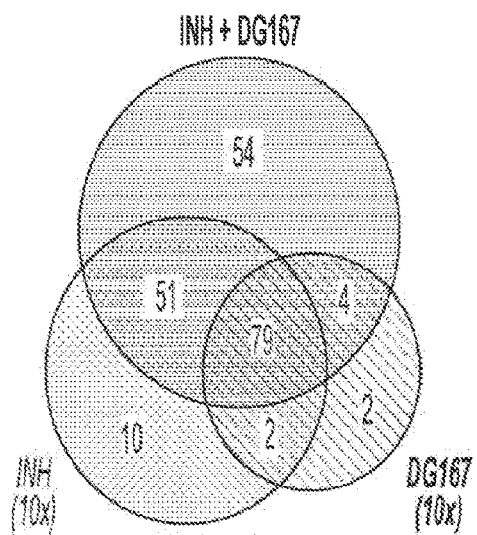

RNAseq analysis was performed to identify pathways that were uniquely activated by dual treatment with DG167 and INH compared to the pathways activated by treatment with either drug alone. The goal was to gain insights into the mechanisms underlying the synergistic lethality that was only observed after simultaneous treatment with both drugs. Single drug treatment with either INH or DG167 strongly induced expression of kasA, kasB, acpM genes, the iniBAC operon, and significantly altered the transcription of other genes known to be modulated by INH (Alland, D., et al., *Proc Natl Acad Sci USA*, 1998, 95, 13227-13232; Boshoff, H. I., et al., *J Biol Chem*, 2004, 279, 40174-40184; and Vilcheze, C., and Jacobs, W. R., Jr., *Microbiol Spectr*, 2014, 2, MGM2-0014-2013) (Table S2). With respect to the dual treatment with DG167 and INH, all but six of the genes that were differentially expressed by DG167 treatment were also differentially expressed by INH treatment, further supporting the hypothesis that DG167 and INH both inhibit targets essential for the same biosynthetic pathway (FIG. 5B). As expected, dual treatment with DG167 and INH altered the expression of almost all (79) of the genes that were differentially expressed by treatment with each drug alone. However, a surprisingly large number of 54 additional genes were differentially expressed only in the dual-treated cultures (FIG. 5B). These "unique, dual-drug modulated" genes were not expressed in either of the cultures that were treated with DG167 or INH as mono-therapy; thus, the differential expression of these 54 genes correlated with synergistic lethality, i.e., a loss of persisters and culture sterilization rather than with drug exposure. Thirty-two of the unique dual-drug modulated genes were up-regulated. This set of up-regulated genes was enriched in oxidoreductases and putative transposase elements. Twenty-two of the unique dual-drug modulated genes were down-regulated. This set of down-regulated genes was enriched for chaperones (groEL1, groEL2 and groES), that are typically up-regulated after treatment with bacteriostatic drugs (Belenky, P., et al., *Cell Rep*, 2015, 13, 968-980; Dwyer, D. J., et al., *Mol Cell*, 2002, 46, 561-572; and Lobritz, M. A., et al., *Proc Natl Acad Sci USA*, 2015, 112, 8173-8180) and are also up-regulated in *M. tuberculosis* persisters during INH exposure (Jain et al., 2016). Together, these results strongly suggest that combined treatment with both DG167 and INH activates a cellular response associated with loss of persistence and induction of cidality that is distinct from the cellular response induced by single drug treatment.

DG167 Profiling.

DG167 was profiled for desirable drug-like and pharmacokinetic properties. DG167 had good selectivity index (SI=CC50/MIC) of 59 with Vero cells. The kinetic solubility in pH 7.4 phosphate-buffered saline (PBS) was 324 µM. The Caco-2 permeabilities (PA-B and PB-A) were 71.8×10−6 and 45.6×10−6 cm/s, respectively. Cytochrome P450 (CYP) inhibition studies demonstrated DG167 did not significantly inhibit CYP enzymes except CYP2C19 ($IC_{50}$=12 µM), and hERG inhibition ($IC_{50}$>20 µM) was also ruled out. Mouse liver microsome (MLM) stability was suboptimal with a $t_{1/2}$=10.1 min. However, the MLM $t_{1/2}$ in the absence of NADPH (to exclude oxidative metabolism) was >300 min. MLM-generated metabolites were examined through mass-spectrometry to identify metabolic liabilities and improve MLM stability. A de-methylated species, corresponding to loss of the 1-methyl group, predominated among the metabolites. When synthesized (Example 1), lacked activity against *M. tuberculosis* (MIC>100 µM), suggesting a metabolic liability at a position that is necessary for whole-cell activity. Promisingly, DG167 accumulated in a dose-dependent manner in *M. tuberculosis* cells and the de-methylated form was not detected, indicating that DG167 is not inactivated by de-methylation inside the bacteria. The inactive des-methyl analog (Example 1) also showed dose-dependent accumulation inside *M. tuberculosis* confirming that intact DG167 was essential for target inhibition and whole-cell activity (de Carvalho, et al., *ACS Med Chem Lett*, 2011, 2, 849-854).

Synthesis of DG167 and Analogs.

The synthesis of DG167 and a focused series of analogs is depicted in FIG. 7. To address the primary metabolic stability of demethylation, a series of N1-substituted indazoles was synthesized and evaluated for anti-tubercular activity and MLM stability. In comparison to DG167, longer or branched alkyl chains with the exception of an ethyl group at the N1 position had unfavorable effects on both activity and MLM $t_{1/2}$. The trideuteriomethyl analog Example 29 offered an improvement in metabolic stability ($t_{1/2}$=16.8 min). Since, Example 29 was a close analog of DG167, its co-crystal structure with KasA was also determined. It also exhibited a binary binding mode consistent with DG16. Analogs featuring replacement of the 6-position sulfonamide with functional groups like carbamate, amide, amine, and urea/thiourea, while retaining the 1-N-methyl group, were synthesized and assayed. Amongst them only 1-n-butyl-3-(1-methyl-1H-indazol-6-yl)thiourea (Example 33) demonstrated modest activity (MIC=3.1 µM). N-methylation of the sulfonamide NH of DG167 (Example 32) resulted in loss of activity. Based on the above results, N1-methyl substitution and a 6-sulfonamide were identified as significant elements for whole-cell efficacy. Subsequently, the sulfonamide n-butyl substituent was truncated or cyclized. Again, a loss of whole-cell activity was noted. Furthermore, the significant loss of whole-cell efficacy for analogs with branched alkyl sulfonamide substituents (i.e., Examples 15-18) hinted at the specific steric requirements of the target enzyme binding site. While the n-hexyl sulfonamide analog Example 12 was inactive, the elongation of n-butyl to n-pentyl chain at the $R^2$ position increased the activity over the parent by twofold when $R^1$=methyl (Example 11) as well as $d_3$-methyl (Example 30). Finally, the indazole's pyrazole unit was transposed to afford Example 41 that demonstrated a 2× improvement in whole-cell activity.

Mouse Pharmacokinetic Profile and Dose Tolerability.

Figure 8:
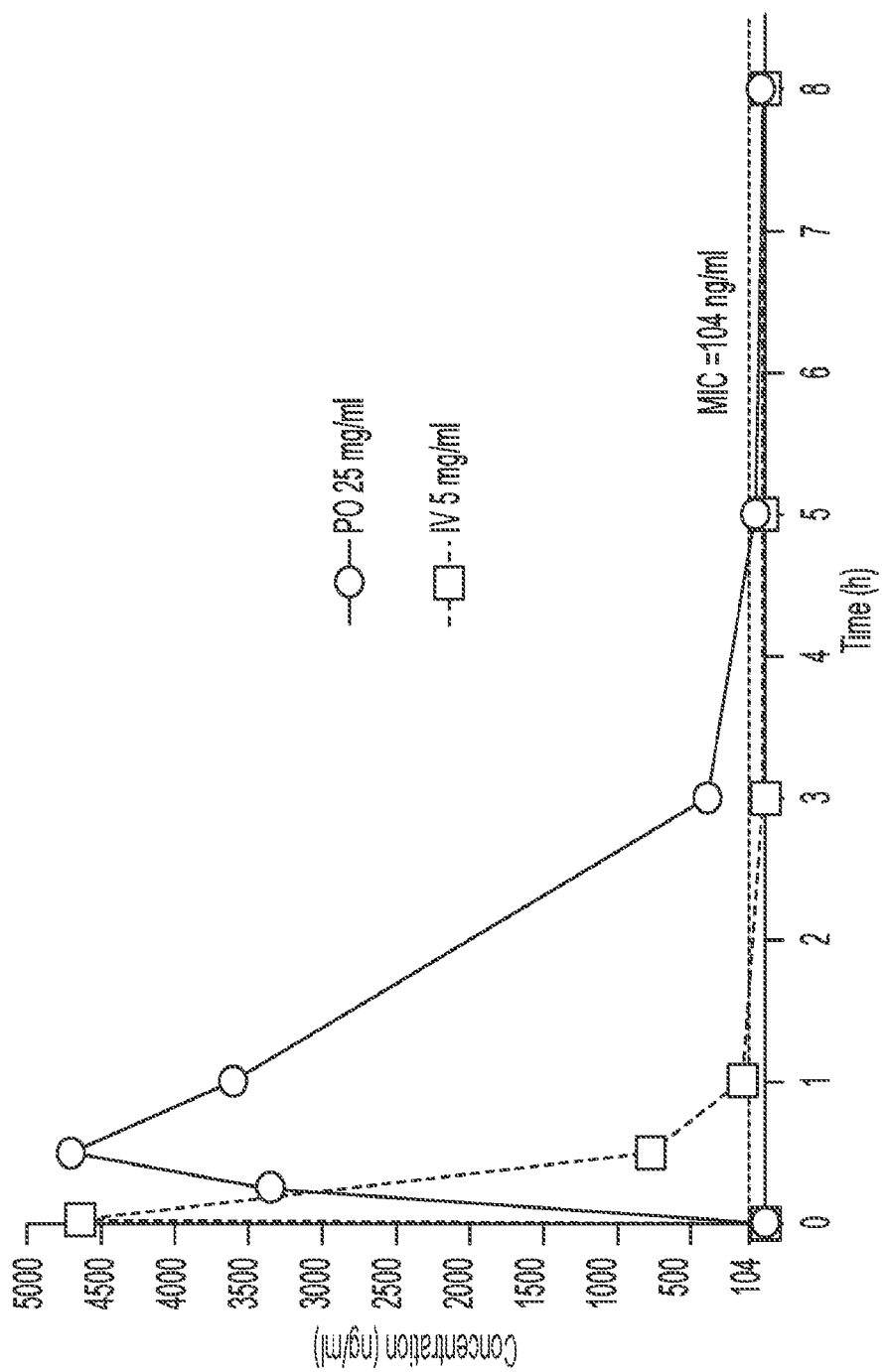

PK profiling was performed to facilitate in vivo efficacy studies. The PK profile of DG167 administered as a single oral dose of 25 mg/kg revealed promising oral bioavailability (92.3%) and plasma levels (AUC0-t of 8083.96 h*ng/m. Plasma levels were maintained above the MIC for over 4 hours (FIG. 8). When IV dosed at 5 mg/kg, the half-life was 0.33 h. A dose escalation study was performed at 50, 100, 250, and 500 mg/kg where the mice were monitored for 8 hours. Both the 50 and 100 mg/kg doses were well tolerated. At higher doses, the mice exhibited heavy breathing, hunched posture and decreased activity. Dose tolerability studies performed for 5 d at 50 mg/kg, 100 mg/kg and combination of DG167 (100 mg/kg) with INH (25 mg/kg) did not show any behavioral changes or weight loss and normal liver pathology was observed (Table 4, FIG. 9).

DG167 and INH Exhibited In Vivo Synergy.

Figure 5C:
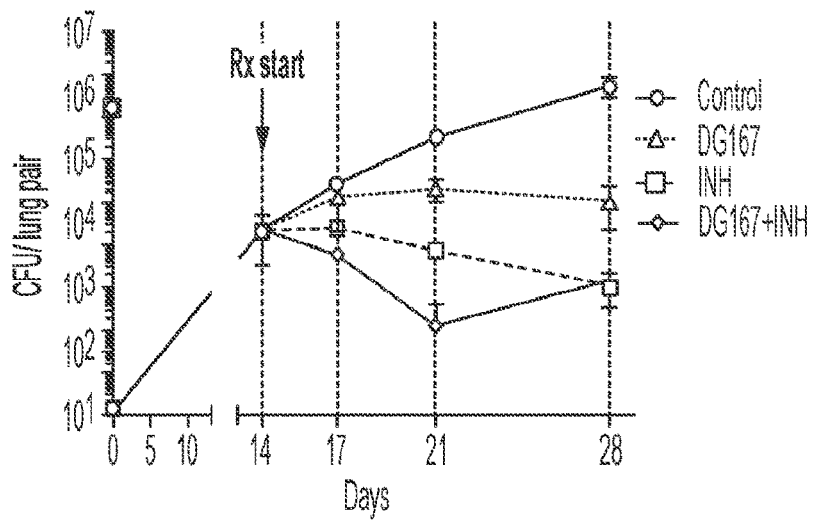
Figure 6A:
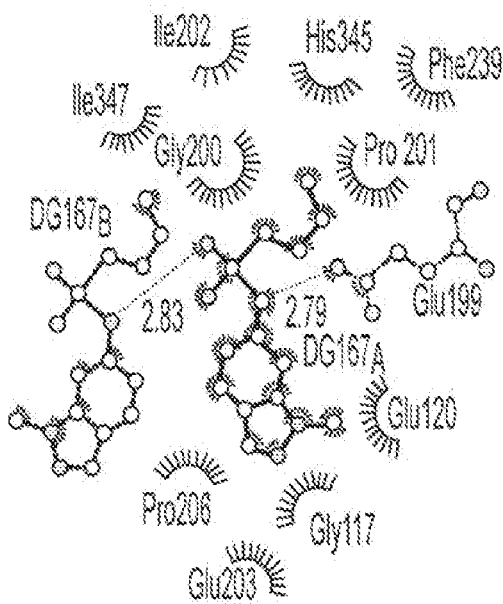
Figure 6B:
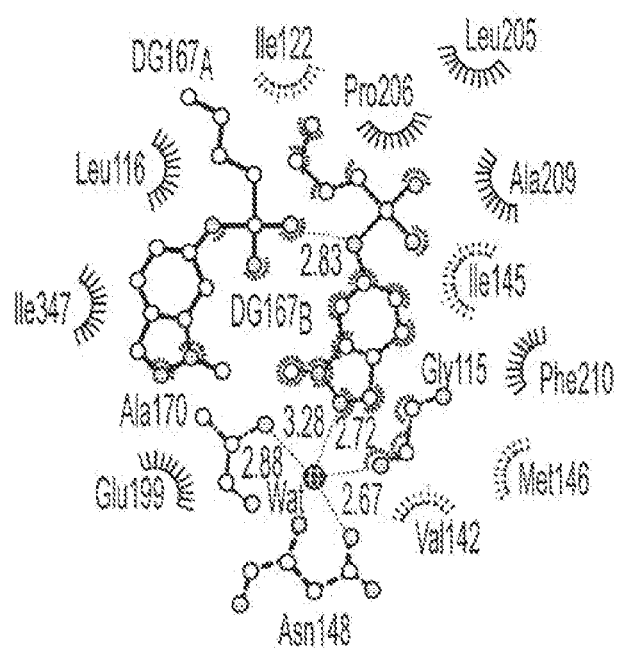
Figure 6C:
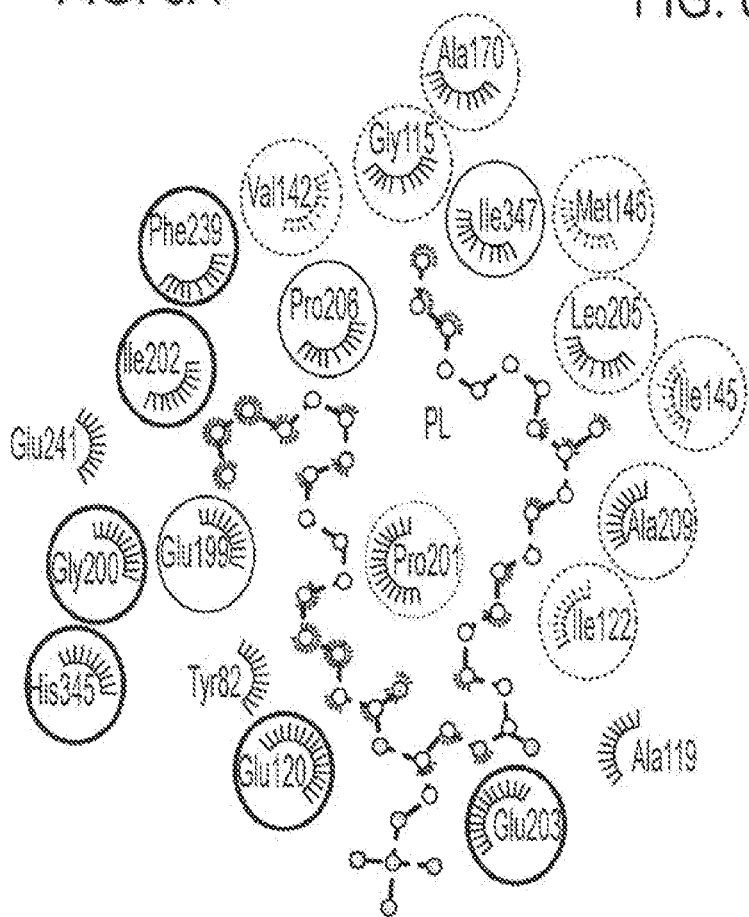

DG167 was studied in an acute murine infection model to determine its efficacy against *M. tuberculosis* both alone and in combination with INH. INH is highly active against *M. tuberculosis* in the acute model, typically showing rapid clearance with 2 weeks of treatment. Therefore, treatment efficacy at the earlier (day 3 and day 7 post-treatment) time points was also studied. DG167 showed 99% reduction in bacterial burden (>2 $\log_{10}$) over 2 weeks (FIG. 5C). Consistent with the in vitro bactericidal studies, the combined treatment of INH with DG167 produced a more rapid reduction in *M. tuberculosis* CFU than either INH or DG167 alone during the two early time points. These data further emphasize the potential benefits for treating TB with INH combined with and a KasA inhibitor.

DISCUSSION

The results above demonstrate that DG167 inhibits mycolic acid biosynthesis by targeting KasA, an essential member of the FAS-II complex in *M. tuberculosis*. DG167 possessed in vitro activity comparable to INH and it targets the same cyclic pathway that produces long chain mycolic acids. Both INH and DG167 show similar three-phase kill curves in vitro, characterized by an initial killing phase followed by a plateau in CFUs and finally outgrowth of both drug susceptible and resistant bacteria. Combined treatment with both INH and DG167 eliminated the undesirable second and third phases and substantially enhanced bactericidal activity, leading to complete sterilization of the bacterial cultures. Synergistic lethality has been used to describe the situation where two bacteriostatic drugs exhibit bactericidal properties when used together (Malik, M., et al., *J Antimicrob Chemother*, 2014, 69, 3227-3235). This term is also appropriate to describe the combined effect of DG167 and INH on *M. tuberculosis* (Jain, P., et al., *MBio*, 2016, 7).

The results above suggest that dual treatment with DG167 and INH is likely to activate intrabacterial processes that could be associated with enhanced cidality. Transcriptional analysis revealed that the co-treatment differentially expressed a unique set of genes that were not expressed by individual drug treatment. The pattern of genes differentially expressed by dual INH/DG167 treatment compared to treatment with either compound individually, including the induction of oxidoreductases and nitrate reductase, and the suppression of molecular chaperones, suggests that dual treatment activates bactericidal and represses persistence mechanisms within the cell. This is supported by studies in *E. coli* where bactericidal drugs develop common metabolic signatures after the first 30 minutes of treatment such as elevation of central carbon metabolites, breakdown of the nucleotide pool and elevated redox state, i.e., increases in respiration. This signature differs from a signature common to bacteriostatic drugs, e.g., accumulation of metabolites that feed the electron transport chain and suppress respiration (Belenky, P., et al., *Cell Rep*, 2015, 13, 968-980; and Lobritz, M. A., et al., *Proc Natl Acad Sci USA*, 2015, 112, 8173-8180).

As described here and by others (Abrahams, K. A., et al., *Nat Commun* 7, 2016, 12581), DG167 has a number of favorable PK-PD properties including high potency, solubility, selectivity and low protein binding, suggesting that this molecule is a promising drug discovery lead. However, DG167 has relatively poor MLM stability, which requires improvement. Indeed, DG167 differs from other previously described KasA inhibitors such as TLM and its analogs (e.g., TLM5) that function by binding to the KasA catalytic site. Instead, DG167 demonstrates a unique property for an antibacterial in that two DG167 molecules bind to nonidentical and non-overlapping surfaces of their target. Furthermore, $DG167_A$ and $DG167_B$ form an intermolecular hydrogen bond. It is also important to note that the KasA biological unit is a homo-dimer, and, as observed in the crystal structure via the application of crystallographic symmetry, there are four molecules of DG167 bound per biological KasA homo-dimer. DG167 binding stabilizes the KasA acyl channel flaps that are otherwise disordered in the absence of PL or DG167. In addition to interacting with their respective KasA, $DG167_{B'}$ interacts with the KasA acyl channel flap, and DG167B interacts with the KasA' acyl channel flap. Similarly, the KasA acyl channel flaps are ordered in the KasA-Example 41 crystal structure, and Example 41 does not make contacts across the dimer interface. Thus, it seems that the requirement for KasA acyl channel flap stabilization is acyl channel occupancy, and it seems likely that flap stabilization contributes allosterically to the binding of DG167 or Example 41 to KasA. In addition, while there are two bound DG167 molecules in the KasA-$DG167_2$ structure, it is likely that the binding of either DG167 molecule would be sufficient to block acyl chain elongation. This is supported by the fact that the DG167 analog Example 41 is an active inhibitor that binds only once to the acyl channel in a conformation similar to $DG167_A$.

The results above also reveal other unique features of DG167, which might prove useful in the design of KasA inhibitors. In current models, acyl-AcpM drives a conformational change in Phe404 that not only activates catalysis by triggering proton transfer from Cys171 to His311, but also permitting acyl chain access to the acyl channel and causing the rearrangement of additional gatekeeper residues. In the KasA-$DG167_2$ structure, Phe404 is in the closed conformation, i.e., acyl chain is excluded from entering the channel. This is believed to be the first time KasA was shown to bind ligand (e.g., inhibitor or PL) while Phe404 is in the closed conformation. Moreover, it is clear that DG167 and acyl chain could not bind simultaneously to KasA. Therefore, DG167 would bind preferentially to non-acylated KasA, which distinguishes DG167 from previously identified KasA inhibitors that bind preferentially to acylated KasA. This is, in part, what makes DG167 unique from cellular free fatty acids, which could, in theory, disrupt KasA function similarly to DG167 if binding were promiscuous. While KasA has evolved mechanisms to exclude free fatty acids from entering the acyl channel via the phosphopantetheine tunnel and the surface near the disordered flaps, DG167 circumvents the requirement for both AcpM and the opening of gatekeeper residue Phe404.

The conformational constraints and molecular interactions that govern the interactions between DG167 and KasA also suggest modifications that could either improve the potency or permit modifications that increase metabolic stability of the current DG167 lead. In fact, the observed SAR trend of the initially synthesized analogs can be explained based on the KasADG167 crystal structure. Consistent with the two DG167 molecules interacting via a hydrogen bond formed between the sulfonamide oxygen on DG167A and the sulfonamide NH of DG167B, methylation of this nitrogen (Compound 33) resulted in a loss of activity. These substitutions for the sulfonamide would also seem likely to significantly alter placement of the pendant alkyl chain. Carbamate, amide, amine, and urea/thiourea functionalities at the 6-position of the indazole also disrupt this intermolecular H-bonding interaction and lead to abrogation of activity. Truncation of the sulfonamide alkyl chain (Examples 7-9) or adding bulky/branched substituents (Example 10 and Examples 15-28) may disrupt placement of the acyl chain pocket formed by the residues Gly200, Ile202, Pro206, Phe239, His345, and Ile347 and thereby reduce potency. Example 13, with a terminal cyano group, retains some activity (MIC=3.1 µM) due to the favorable interactions with the hydrophobic acyl chain pocket, whereas the terminal methoxy group of Example 14 (MIC>100 µM) may introduce clashes between lone pairs on the ether oxygen and proximal hydrophobic side chains (Gly200, Ile202, Pro206, Phe239). Interestingly, Example 11 and Example 30, with an n-pentyl sulfonamide, offer increased hydrophobic interactions, presenting an explanation for the 2-fold increase in potency over DG167.

KasA is a valid drug discovery target within *M. tuberculosis* with a potential to rapidly kill *M. tuberculosis* and perhaps shorten treatment in clinical TB, especially when used in combination with INH.

Example 55

The following illustrate representative pharmaceutical dosage forms, containing a compound of formula I ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X= (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X= (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Tri chi oromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

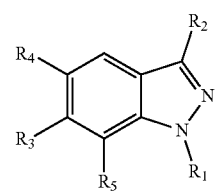

or a salt thereof, wherein:
$R^1$ is H;
$R^2$ is H, halo, or $(C_1-C_4)$alkyl that is optionally substituted with one or more halo;

$R^3$ is H and $R^4$ is $-N(R^a)SO_2R^c$;
$R^5$ is H, $(C_1-C_4)$alkyl, or halo;
each $R^a$ is independently H or $(C_1-C_4)$alkyl; and
$R^c$ is $(C_3-C_6)$cycloalkyl, or $(C_2-C_6)$alkyl, wherein any $(C_3-C_6)$cycloalkyl and $(C_2-C_6)$alkyl is optionally substituted with one or more groups independently selected from the group consisting of halo, $(C_3-C_6)$cycloalkyl, phenyl, $(C_1-C_4)$alkoxy, trifluoromethyl, and cyano.

2. The compound or salt of claim 1, which is a compound of formula (Ie):

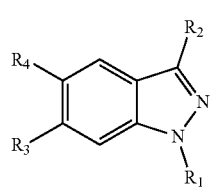

(Ie)

wherein $R^2$ is H, halo, or $(C_1-C_4)$alkyl or a salt thereof.

3. The compound or salt of claim 1, wherein $R^2$ is H or methyl.

4. The compound or salt of claim 1, wherein
$R^1$ is H;
$R^2$ is H, $(C_1-C_4)$alkyl, or halo;
$R^3$ is H and $R^4$ is $-N(R^a)SO_2R^c$;
each $R^a$ is independently H or $(C_1-C_4)$alkyl; and
$R^c$ is $(C_3-C_6)$cycloalkyl, or $(C_2-C_6)$alkyl, wherein any $(C_3-C_6)$cycloalkyl and $(C_2-C_6)$alkyl is optionally substituted with one or more groups independently selected from the group consisting of halo, and cyano.

5. The compound or salt of claim 1, wherein $R^c$ is $(C_3-C_6)$alkyl that is optionally substituted with one or more groups independently selected from the group consisting of halo and cyano.

6. A compound or salt that is selected from the group consisting of:

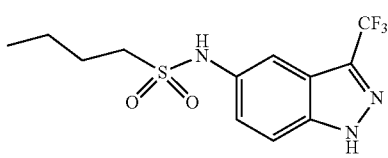

51

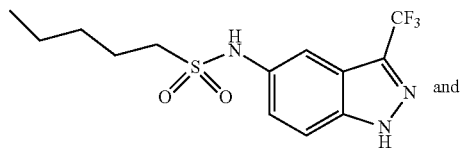

52 and

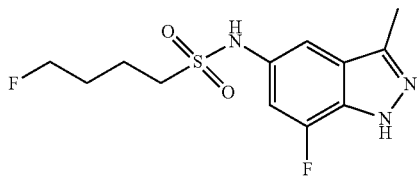

53 and salts thereof.

7. The compound,

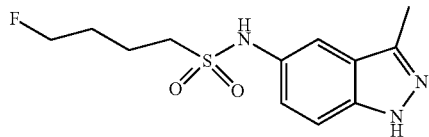 [SMILES: Cc1n[nH]c2ccc(NS(=O)(=O)CCCCF)cc12]

or a salt thereof.

8. A pharmaceutical composition comprising a compound as described in claim 1, or a pharmaceutically acceptable salt thereof, and a pharmaceutically acceptable excipient.

9. The composition of claim 8, that further comprises another antibacterial drug.

10. The composition of claim 9, wherein the other antibacterial drug is isoniazid.

11. A pharmaceutical composition comprising a compound as described in claim 6, or a pharmaceutically acceptable salt thereof, and a pharmaceutically acceptable excipient.

12. A pharmaceutical composition comprising a compound as described in claim 7, or a pharmaceutically acceptable salt thereof, and a pharmaceutically acceptable excipient.

* * * * *

UNITED STATES PATENT AND TRADEMARK OFFICE
CERTIFICATE OF CORRECTION

PATENT NO. : 11,186,549 B2
APPLICATION NO. : 16/642817
DATED : November 30, 2021
INVENTOR(S) : Joel S. Freundlich et al.

It is certified that error appears in the above-identified patent and that said Letters Patent is hereby corrected as shown below:

In the Specification

Column 1, Lines 12-15, please delete "This invention was made with government support under 1U19AI109713 , R21AI111647 , and R33AI1167 awarded by the National Institutes of Health . The government has certain rights in the invention ." and insert -- This invention was made with government support under grant numbers AI011167, AI109713, AI111647, HL150852 awarded by the National Institutes of Health. The government has certain rights in the invention. -- therefor.

Signed and Sealed this
Fourth Day of July, 2023

Katherine Kelly Vidal
*Director of the United States Patent and Trademark Office*